US011628170B2

(12) United States Patent
Bordbar

(10) Patent No.: US 11,628,170 B2
(45) Date of Patent: *Apr. 18, 2023

(54) TREATING EXTRAPYRAMTDAL SYNDROME USING TRAPIDIL

(71) Applicant: Sinopia Biosciences, Inc., San Diego, CA (US)

(72) Inventor: Aarash Bordbar, San Diego, CA (US)

(73) Assignee: SINOPIA BIOSCIENCES, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/503,128

(22) Filed: Jul. 3, 2019

(65) Prior Publication Data

US 2019/0328741 A1    Oct. 31, 2019

Related U.S. Application Data

(63) Continuation of application No. 15/962,999, filed on Apr. 25, 2018, now Pat. No. 10,350,212, which is a continuation of application No. PCT/US2017/025788, filed on Apr. 3, 2017.

(60) Provisional application No. 62/317,983, filed on Apr. 4, 2016.

(51) Int. Cl.

| A61K 31/519 | (2006.01) |
| A61K 9/00 | (2006.01) |
| A61K 45/06 | (2006.01) |
| A61K 31/53 | (2006.01) |
| A61K 31/5377 | (2006.01) |
| A61P 25/14 | (2006.01) |
| A61P 25/18 | (2006.01) |
| A61K 31/198 | (2006.01) |

(52) U.S. Cl.
CPC .......... *A61K 31/519* (2013.01); *A61K 9/0019* (2013.01); *A61K 9/0053* (2013.01); *A61K 31/198* (2013.01); *A61K 31/53* (2013.01); *A61K 31/5377* (2013.01); *A61K 45/06* (2013.01); *A61P 25/14* (2018.01); *A61P 25/18* (2018.01)

(58) Field of Classification Search
CPC .. A61K 31/519; A61K 9/0019; A61K 9/0053; A61K 31/198; A61K 31/53; A61K 31/5377; A61K 45/06; A61P 25/14; A61P 25/18

See application file for complete search history.

(56) References Cited

U.S. PATENT DOCUMENTS

| 4,327,725 A | 5/1982 | Cortese et al. |
| 4,624,848 A | 11/1986 | Lee |
| 4,739,044 A | 4/1988 | Stabinsky |
| 4,757,141 A | 7/1988 | Fung et al. |
| 4,843,155 A | 6/1989 | Chomczynski |
| 4,968,509 A | 11/1990 | Radebaugh et al. |
| 5,348,853 A | 9/1994 | Wang et al. |
| 5,384,261 A | 1/1995 | Winkler et al. |
| 5,445,934 A | 8/1995 | Fodor et al. |
| 5,456,923 A | 10/1995 | Nakamichi et al. |
| 5,461,140 A | 10/1995 | Heller et al. |
| 5,516,527 A | 5/1996 | Curatolo |
| 5,567,583 A | 10/1996 | Wang et al. |
| 5,622,721 A | 4/1997 | Dansereau et al. |
| 5,677,195 A | 10/1997 | Winkler et al. |
| 5,686,105 A | 11/1997 | Kelm et al. |
| 5,700,410 A | 12/1997 | Nakamichi et al. |
| 5,708,153 A | 1/1998 | Dower et al. |
| 5,738,874 A | 4/1998 | Conte et al. |
| 5,744,305 A | 4/1998 | Fodor et al. |
| 5,770,358 A | 6/1998 | Dower et al. |
| 5,770,722 A | 6/1998 | Lockhart et al. |
| 5,789,162 A | 8/1998 | Dower et al. |
| 5,800,992 A | 9/1998 | Fodor et al. |
| 5,854,033 A | 12/1998 | Lizardi |
| 5,858,401 A | 1/1999 | Bhalani et al. |
| 5,869,717 A | 2/1999 | Frame et al. |
| 5,874,219 A | 2/1999 | Rava et al. |
| 5,977,175 A | 11/1999 | Lin |
| 5,994,056 A | 11/1999 | Higuchi |
| 6,015,578 A | 1/2000 | Walch |
| 6,020,135 A | 2/2000 | Levine et al. |
| 6,033,854 A | 3/2000 | Kurnit et al. |
| 6,033,860 A | 3/2000 | Lockhart et al. |
| 6,040,138 A | 3/2000 | Lockhart et al. |
| 6,040,193 A | 3/2000 | Winkler et al. |

(Continued)

FOREIGN PATENT DOCUMENTS

| EP | 0301423 A1 | 2/1989 |
| WO | WO-9309781 A1 | 5/1993 |

(Continued)

OTHER PUBLICATIONS

Nagakawa et al (Year: 1984).*
Giessler et al (Year: 1987).*
Riedel et al (Year: 1987).*
Osinski (Year: 2000).*

(Continued)

*Primary Examiner* — Jeffrey S Lundgren
*Assistant Examiner* — Ibrahim D Bori
(74) *Attorney, Agent, or Firm* — Wilson Sonsini Goodrich & Rosati

(57) ABSTRACT

Disclosed herein are methods, pharmaceutical combinations, or kits for the prevention or treatment of extrapyramidal syndromes, for example, dyskinesia, dystonia, akathisia, or drug-induced Parkinsonism, with the administration of a therapeutic effective amount of Trapidil, a derivative, a metabolite, a prodrug, an analog, or a pharmaceutically acceptable salt thereof.

23 Claims, 5 Drawing Sheets

(56) References Cited

U.S. PATENT DOCUMENTS

| | | |
|---|---|---|
| 6,171,785 B1 | 1/2001 | Higuchi |
| 6,344,316 B1 | 2/2002 | Lockhart et al. |
| 6,369,065 B1 | 4/2002 | Chatelain et al. |
| 6,465,014 B1 | 10/2002 | Moroni et al. |
| 6,667,048 B1 | 12/2003 | Lambert et al. |
| 6,932,983 B1 | 8/2005 | Straub et al. |
| 6,960,563 B2 | 11/2005 | Egbaria et al. |
| 10,350,212 B2 | 7/2019 | Bordbar |
| 2006/0166972 A1 | 7/2006 | Conn et al. |
| 2007/0117765 A1 | 5/2007 | Sauve et al. |
| 2008/0242657 A1 | 10/2008 | Marino et al. |
| 2009/0192111 A1 | 7/2009 | Bader et al. |
| 2012/0208706 A1 | 8/2012 | Downing et al. |

FOREIGN PATENT DOCUMENTS

| | | | |
|---|---|---|---|
| WO | WO-2014019979 A1 * | 2/2014 | ............ A61P 21/00 |
| WO | WO-201 7059113 A1 | 4/2017 | |
| WO | WO-201 7176652 A2 | 10/2017 | |

OTHER PUBLICATIONS

Heiman et al (Year: 2014).*
Giorgi et al (Year: 2008).*
Sharma et al (Year: 2013).*
Heiman (Year: 2014).*
Sharma (Year: 2013).*
Giessler (Year: 1987).*
Bethke et al (Year: 1991).*
KR20150015854A, Machine Translation (Year: 2015).*
Giorgi (Year: 2008).*
Raubach (Year: 1997).*
Agrawal, et al. Site-specific functionalization of oligodeoxynucleotides for non-radioactive labelling. Tetrahedron Letters. 1990 31:1543-1546.
Barany. Genetic disease detection and DNA amplification using cloned thermostable ligase. PNAS USA 88:189-193 (1991).
Cao et al. Striatal overexpression of DeltaFosB reproduces chronic levodopa-induced involuntary movements. J Neurosc 30(21):7335-7343 (2010).
Caruthers. Gene synthesis machines: DNA chemistry and its uses. Science 230(4723):281-285 (1985).
Cenci et al. Ratings of L-DOPA-Induced Dyskinesia in the Unilateral 6-OHDA Lesion Model of Parkinson's Disease in Rats and Mice. Curr Protoc Neurosci Chapter 9:Unit 9.25 (23 pgs) (2007).
Deslauriers et al. Implication of the ERK/MAPK pathway in antipsychotics-induced dopamine D2 receptor upregulation and in the preventive effects of (+/-)-alpha-lipoic acid in SH-SY5Y neuroblastoma cells. J Mol Neurosci 52(3):378-383 (2014).
Giusti et al. Synthesis and characterization of 5'-fluorescent-dye-labeled oligonucleotides. PCR Methods Appl. 2(3):223-227 (1993).
Guatelli et al. Isothermal, in vitro amplification of nucleic acids by a multienzyme reaction modeled after retroviral replication. PNAS USA 87(5):1874-1878 (1990).
Gupta et al. A general method for the synthesis of 3'-sulfhydryl and phosphate group containing oligonucleotides. Nucleic Acids Res. 19(11):3019-3025 (1191).
Heid et al. Real time quantitative PCR. Genome Res. 6(10):986-994 (1996).
Heinroth et al. Influence of Trapidil derivatives on arachidonic acid- and prostaglandin endoperoxide analogue-induced platelet aggregation and thromboxane A2 formation. Biomedica biochimica acta 43(8-9):S389-392 (Abstract only) (1983).
Heinroth-Hoffmann et al. Influence of Trapidil and Trapidil Derivatives on the Content of Cyclic Nucleotides in Human Intima Cells Cultured from Atherosclerotic Plaques. Drug Development Res 19(3):321-327 (1990).
Kwoh et al. Transcription-based amplification system and detection of amplified human immunodeficiency virus type 1 with a bead-based sandwich hybridization format. PNAS USA 86(4):1173-1177 (1989).
Lamb et al. The Connectivity Map: Using Gene-Expression Signatures to Connect Small Molecules, Genes, and Disease. Science 313:1929-1935 (2006).
Liberman et al. Pharmaceutical Dosage Forms. 2nd Ed. 1:209-214 (1990).
Lizardi et al. Exponential amplification of recombinant-RNA hybridization probes. Nature Biotechnology 6:1197-1202 (1988).
Nelson et al. Bifunctional oligonucleotide probes synthesized using a novel CPG support are able to detect single base pair mutations. Nucleic Acids Res. 17(18):7187-7194 (1989).
Nguyen et al. Differential expression of c-fos and zif268 in rat striatum after haloperidol, clozapine, and amphetamine. PNAS USA 89(10):4270-4274 (1992).
Nogrady. Medicinal Chemistry a Biochemical Approach, Oxford University Press, New York, pp. 388-392 (1985).
PCT/US2018/025788 International Search Report and Written Opinion dated Apr. 9, 2018.
Pfeifer et al. Biotransformation of the Trapidil (rocornal) derivative AR 12463 in the rat. Die Pharmazie 45(8), 609-614 (1990) (English Abstract).
Ploem. Chapter 1: Fluorescence Microscopy. Fluorescent and Luminescent Probes for Biological Activity Mason, T. G. Ed., Academic Press, Landon, pp. 1-11 (1993).
Santini et al. L-DOPA activates ERK signaling and phosphorylates histone H3 in the striatonigral medium spiny neurons of hemiparkinsonian mice. J Neurochem 108(3):621-633 (2009).
Saulnier et al. An Efficient Method for The Synthesis of Guanidino Prodrugs. Bioorganic and Medicinal Chemistry Letters 4(16):1985-1990 (1994).
Silverman et al. Chapter 8: Prodrugs and drug delivery systems. In: The Organic Chemistry of Drug Design and Drug Action. San Diego: Academic Press, Inc. p. 352-401 (1992).
Smith et al. Fluorescence detection in automated DNA sequence analysis, Nature 321:674-679 (1986).
Smith et al. Striatal mRNA expression patterns underlying peak dose L-DOPA-induced dyskinesia in the 6-OHDA hemiparkinsonian rat. Neuroscience 324:238-251 (2016).
Smith et al. The synthesis of oligonucleotides containing an aliphatic amino group at the 5' terminus: synthesis of fluorescent DNA primers for use in DNA sequence analysis. Nucl. Acid Res. 13:2399-2412 (1985).
Stahl et al. Supplementary material—list of pharmaceutically acceptable acids. Handbook of Pharmaceutical Salts (1 pg.) (2002).
Thanvi et al. Levodopa-induced dyskinesia in Parkinson's disease: clinical features, pathogenesis, prevention and treatment. Postgrad Med J. 83(980):384-388 (2007).
Thiirmann et al. Pharmacokinetics of the PDGF-antagonist Trapidil in patients with and without renal impairment. Clin Nephrol 47(2):99-105 (Abstract only) (1997).
U.S. Appl. No. 15/962,999 Office Action dated Jul. 16, 2018.
U.S. Appl. No. 15/962,999 Office Action dated Mar. 8, 2019.
U.S. Appl. No. 15/962,999 Office Action dated Nov. 6, 2018.
Yershov et al. DNA analysis and diagnostics on oligonucleotide microchips. PNAS USA 93(10):4913-4918 (1996).

* cited by examiner

TREATING EXTRAPYRAMIDAL SYNDROME USING TRAPIDIL

CROSS-REFERENCE

This application is a continuation of U.S. application Ser. No. 15/962,999, now U.S. Pat. No. 10,350,212, filed Apr. 25, 2018, which is a continuation of International Application No. PCT/US2017/025788, filed on Apr. 3, 2017, which claims the benefit of U.S. Provisional Application No. 62/317,983, filed Apr. 4, 2016, all of which are incorporated herein by reference in their entireties.

STATEMENT AS TO FEDERALLY SPONSORED RESEARCH

This invention was made with the support of the United States government under Contract number R44GM121117 by the National Institutes of Health. The government has certain rights in this invention.

SUMMARY OF THE DISCLOSURE

Disclosed herein, in certain embodiments, are methods, pharmaceutical combinations, dosage forms, and kits for the treatment of an extrapyramidal syndrome. In some instances, the treatment comprises use of a therapeutic effective amount of Trapidil. In other instances, the treatment comprises use of a therapeutic effective amount of a derivative, a metabolite, a prodrug, an analog, or a pharmaceutically acceptable salt thereof of Trapidil.

Disclosed herein, in certain embodiments, is a method of treating an extrapyramidal syndrome in a subject in need thereof comprising administering to the subject a therapeutic effective dose of Trapidil, a derivative, a metabolite, a prodrug, an analog, or a pharmaceutically acceptable salt thereof. In some instances, the subject is administered with a therapeutic effective dose of Trapidil, a derivative, a metabolite, or a pharmaceutically acceptable salt thereof. In some embodiments, the extrapyramidal syndrome comprises dyskinesia, dystonia, akathisia, or drug-induced Parkinsonism. In some embodiments, the dyskinesia is tardive dyskinesia (TD). In some embodiments, the dyskinesia is levodopa-induced dyskinesia (LID). In some embodiments, the dyskinesia is diphasic dyskinesia or peak-dose dyskinesia. In some embodiments, the dystonia is generalized dystonia, focal dystonia, segmental dystonia, or acute dystonia. In some embodiments, the akathisia is acute akathisia, chronic akathisia, pseudoakathisia, or withdrawal or "rebound" akathisia. In some embodiments, Trapidil is N,N-diethyl-5-methyl-[1,2,4]triazolo[1,5-a]pyrimidin-7-amine. In some embodiments, the derivative comprises any of the following compounds:

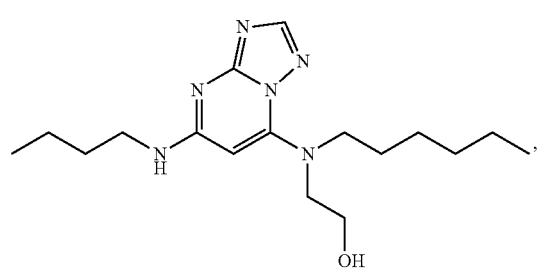
(AR12455)

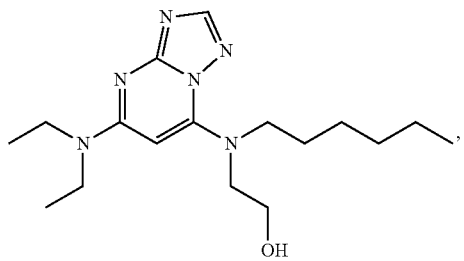
(AR12456)

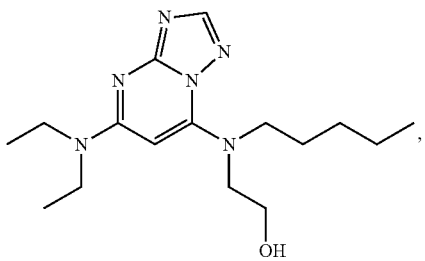
(AR12460)

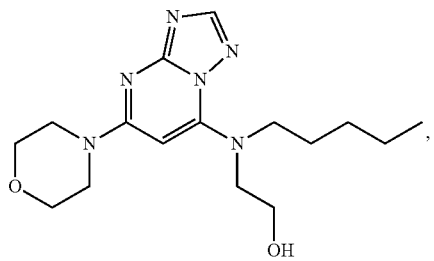
(AR12463)

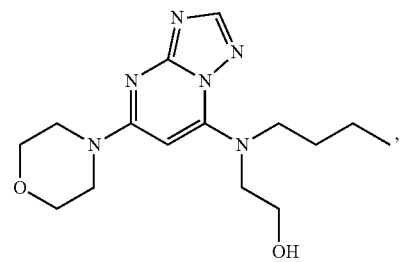
(AR12464)

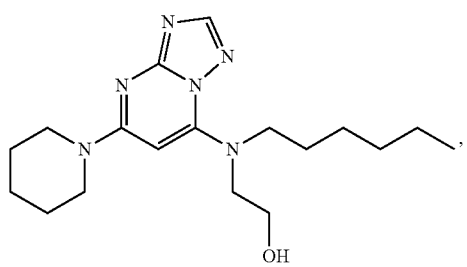
(AR12465)

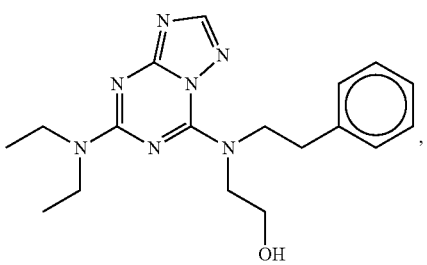
(AR12565)

In some embodiments, the metabolite comprises desethyl-trapidil, 5-piperidin-4'-olyl-7-[N-pentyl-N-(beta-hydroxy-ethyl)]amino-s-triazolo[1,5-a]pyrimidine, 5-piperidin-4'-olyl-7-[N-pent-4-olyl-N-(beta-hydroxyet hyl)]amino-s-triazolo[1,5-a]pyrimidine, hydroxy- or ketopentyl derivatives, piperidinoles or piperidinones, or either of the following compounds:

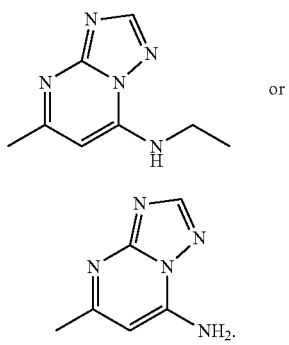

(TP-1)

or (TP-2)

In some embodiments, the pharmaceutically acceptable salt comprises salts with hydrochloric acid, hydrobromic acid, hydroiodic acid, sulfuric acid, nitric acid, ocalic acid, malonic acid, or tartaric acid. In some embodiments, Trapidil, a derivative, a metabolite, a prodrug, an analog, or a pharmaceutically acceptable salt thereof is administered orally. In some embodiments, Trapidil, a derivative, a metabolite, a prodrug, an analog, or a pharmaceutically acceptable salt thereof is administered intravenously or subcutaneously. In some embodiments, the method further comprises administering an additional therapeutic agent. In some embodiments, the additional therapeutic agent comprises clonazepam, Ginkgo biloba, clozapine, risperidone, quetiapine, vitamin E, levodopa, benzodiazepines, botulinum toxin, reserpine, tetrabenazine, propranolol, dopamine-depleting agents, ondansetron, zotepine, aripiprazole, zopiclone, zonisamide, trihexyphenidyl (Broflex), biperiden, procyclidine, diazepam, baclofen, tizanidine, carbamazepine, gabapentin, lorazepam, mianserin, cyproheptadine, mirtazapine, benztropin, trihexyphenidyl, carbidopa, ropinirole, pramipexole, bromocriptine, selegiline, rasagiline, ziprasidone, olanzapine, amantadine, valbenazine, dutetrabenazine, or diphenhydramine. In some embodiments, the additional therapeutic agent is administered orally. In some embodiments, the additional therapeutic agent is administered intravenously or subcutaneously. In some embodiments, Trapidil, a derivative, a metabolite, a prodrug, an analog, or a pharmaceutically acceptable salt thereof and the additional therapeutic agent are administered simultaneously. In some embodiments, Trapidil, a derivative, a metabolite, a prodrug, an analog, or a pharmaceutically acceptable salt thereof and the additional therapeutic agent are administered sequentially. In some embodiments, Trapidil, a derivative, a metabolite, a prodrug, an analog, or a pharmaceutically acceptable salt thereof is administered prior to administration of the additional therapeutic agent. In some embodiments, Trapidil, a derivative, a metabolite, a prodrug, an analog, or a pharmaceutically acceptable salt thereof is administered after the administration of the additional therapeutic agent. In some embodiments, the subject is diagnosed with an extrapyramidal syndrome. In some embodiments, the subject exhibits at least one marker that is associated with an extrapyramidal syndrome. In some embodiments, the at least one marker is selected from FOSL2, JUN, JUND, ATF3, SREBF2, INSIG1, MVK, MVD, LDLR, HMGCR, ERK, DUSP14, SQSTM1, IER3, CDKN1A, MYC, and BCL2. In some embodiments, the at least one marker is upregulated. In some embodiments, the at least one marker that is upregulated is selected from FOSL2, JUN, SREBF1, CEBPB, UBC, and ERK. In some embodiments, the at least one marker is downregulated. In some embodiments, the at least one marker is selected from MYC and BCL2. In some embodiments, Trapidil, a derivative, a metabolite, or a pharmaceutically acceptable salt thereof modulates the at least one marker associated with an extrapyramidal syndrome. In some embodiments, the subject has not been diagnosed with an extrapyramidal syndrome. In some embodiments, the subject is a human.

Disclosed herein, in certain embodiments, is a method of preventing an extrapyramidal syndrome in a subject in need thereof comprising administering to the subject a therapeutic effective dose of Trapidil, a derivative, a metabolite, a prodrug, an analog, or a pharmaceutically acceptable salt thereof. In some instances, the subject is administered with a therapeutic effective dose of Trapidil, a derivative, a metabolite, or a pharmaceutically acceptable salt thereof. In some embodiments, the extrapyramidal syndrome comprises dyskinesia, dystonia, akathisia, or drug-induced Parkinsonism. In some embodiments, the dyskinesia is tardive dyskinesia (TD). In some embodiments, the dyskinesia is levodopa-induced dyskinesia (LID). In some embodiments, the dyskinesia is diphasic dyskinesia or peak-dose dyskinesia. In some embodiments, the dystonia is generalized dystonia, focal dystonia, segmental dystonia, or acute dystonia. In some embodiments, the akathisia is acute akathisia, chronic akathisia, pseudoakathisia, or withdrawal or "rebound" akathisia. In some embodiments, Trapidil is N,N-diethyl-5-methyl-[1,2,4]triazolo[1,5-a]pyrimidin-7-amine.

In some embodiments, the derivative comprises AR 12455, AR 12456, AR 12460, AR 12463, AR 12464, AR 12465, AR 12560, or AR 12565. In some embodiments, the metabolite comprises desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyet hyl)]amino-s-triazolo[1,5-a]pyrimidine, hydroxy- or ketopentyl derivatives, piperidinoles or piperidinones, TP1, or TP2. In some embodiments, the pharmaceutically acceptable salt comprises salts with hydrochloric acid, hydrobromic acid, hydroiodic acid, sulfuric acid, nitric acid, ocalic acid, malonic acid, or tartaric acid. In some embodiments, Trapidil, a derivative, a metabolite, a prodrug, an analog, or a pharmaceutically acceptable salt thereof is administered orally. In some embodiments, Trapidil, a derivative, a metabolite, a prodrug, an analog, or a pharmaceutically acceptable salt thereof is administered intravenously or subcutaneously. In some embodiments, the method further comprises administering an additional therapeutic agent. In some embodiments, the additional therapeutic agent comprises clonazepam, Ginkgo biloba, clozapine, risperidone, quetiapine, vitamin E, levodopa, benzodiazepines, botulinum toxin, reserpine, tetrabenazine, propranolol, dopamine-depleting agents, ondansetron, zotepine, aripiprazole, zopiclone, zonisamide, trihexyphenidyl (Broflex), biperiden, procyclidine, diazepam, baclofen, tizanidine, carbamazepine, gabapentin, lorazepam, mianserin, cyproheptadine, mirtazapine, benztropin, trihexyphenidyl, carbidopa, ropinirole, pramipexole, bromocriptine, selegiline, rasagiline, ziprasidone, olanzapine, amantadine, valbenazine, dutetrabenazine, or diphenhydramine. In some embodiments, the additional therapeutic agent is administered orally. In some embodiments, the additional therapeutic agent is administered intravenously or subcutaneously. In some embodiments, Trapidil, a derivative, a metabolite, a prodrug, an analog, or a pharmaceutically acceptable salt thereof and the additional therapeutic agent are administered simultaneously. In some embodiments, Trapidil, a derivative, a metabolite, a prodrug, an analog, or a pharmaceutically acceptable salt thereof and the additional therapeutic agent are administered sequentially. In some embodiments, Trapidil, a derivative, a metabolite, a prodrug, an analog, or a pharmaceutically acceptable salt thereof is administered prior to administration of the additional therapeutic agent. In some embodiments, Trapidil, a derivative, a metabolite, a prodrug, an analog, or a pharmaceutically acceptable salt thereof is administered after the administration of the additional therapeutic agent. In some embodiments, the subject is diagnosed with an extrapyramidal syndrome. In some embodiments, the subject exhibits at least one marker that is associated with an extrapyramidal syndrome. In some embodiments, the at least one marker is selected from FOSL2, JUN, JUND, ATF3, SREBF2, INSIG1, MVK, MVD, LDLR, HMGCR, ERK, DUSP14, SQSTM1, IER3, CDKN1A, MYC, and BCL2. In some embodiments, the at least one marker is upregulated. In some embodiments, the at least one marker that is upregulated is selected from FOSL2, JUN, SREBF1, CEBPB, UBC, and ERK. In some embodiments, the at least one marker is downregulated. In some embodiments, the at least one marker is selected from MYC and BCL2. In some embodiments, Trapidil, a derivative, a metabolite, or a pharmaceutically acceptable salt thereof modulates the at least one marker associated with an extrapyramidal syndrome. In some embodiments, the subject has not been diagnosed with an extrapyramidal syndrome. In some embodiments, the subject is a human.

Disclosed herein, in certain embodiments, is a pharmaceutical combination comprising a therapeutic effective dose of Trapidil, a derivative, a metabolite, a prodrug, an analog, or a pharmaceutically acceptable salt thereof; and an additional therapeutic agent. In some embodiments, Trapidil is N,N-diethyl-5-methyl-[1,2,4]triazolo[1,5-a]pyrimidin-7-amine. In some embodiments, the derivative comprises AR 12455, AR 12456, AR 12460, AR 12463, AR 12464, AR 12465, AR 12560, or AR 12565. In some embodiments, the metabolite comprises desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyet hyl)]amino-s-triazolo[1,5-a]pyrimidine, hydroxy- or ketopentyl derivatives, piperidinoles or piperidinones, TP1, or TP2. In some embodiments, the pharmaceutically acceptable salt comprises salts with hydrochloric acid, hydrobromic acid, hydroiodic acid, sulfuric acid, nitric acid, ocalic acid, malonic acid, or tartaric acid. In some embodiments, the additional therapeutic agent comprises clonazepam, Ginkgo biloba, clozapine, risperidone, quetiapine, vitamin E, levodopa, benzodiazepines, botulinum toxin, reserpine, tetrabenazine, propranolol, dopamine-depleting agents, ondansetron, zotepine, aripiprazole, zopiclone, zonisamide, trihexyphenidyl (Broflex), biperiden, procyclidine, diazepam, baclofen, tizanidine, carbamazepine, gabapentin, lorazepam, mianserin, cyproheptadine, mirtazapine, benztropin, trihexyphenidyl, carbidopa, ropinirole, pramipexole, bromocriptine, selegiline, rasagiline, ziprasidone, olanzapine, amantadine, valbenazine, dutetrabenazine, or diphenhydramine. In some embodiments, Trapidil, a derivative, a metabolite, a prodrug, an analog, or a pharmaceutically acceptable salt thereof is administered orally. In some embodiments, Trapidil, a derivative, a metabolite, a prodrug, an analog, or a pharmaceutically acceptable salt thereof is administered intravenously or subcutaneously. In some embodiments, the additional therapeutic agent is administered orally. In some embodiments, the additional therapeutic agent is administered intravenously or subcutaneously. In some embodiments, Trapidil, a derivative, a metabolite, a prodrug, an analog, or a pharmaceutically acceptable salt thereof and the additional therapeutic agent are administered simultaneously. In some embodiments, Trapidil, a derivative, a metabolite, a prodrug, an analog, or a pharmaceutically acceptable salt thereof and the additional therapeutic agent are administered sequentially. In some embodiments, Trapidil, a derivative, a metabolite, a prodrug, an analog, or a pharmaceutically acceptable salt thereof is administered before the administration of the additional therapeutic agent. In some embodiments, Trapidil, a derivative, a metabolite, a prodrug, an analog, or a pharmaceutically acceptable salt thereof is administered after the administration of the additional therapeutic agent.

Disclosed herein, in certain embodiments, is a dosage combination for use in a treatment of an extrapyramidal syndrome in a subject in need thereof, comprising administering to the subject a therapeutic effective dose of Trapidil, a derivative, a metabolite, a prodrug, an analog, or a pharmaceutically acceptable salt thereof; and an additional therapeutic agent; wherein the therapeutic amount treats the extrapyramidal syndrome in the subject in need thereof. In some embodiments, the extrapyramidal syndrome comprises dyskinesia, dystonia, akathisia, or drug-induced Parkinsonism. In some embodiments, the dyskinesia is tardive dyskinesia (TD). In some embodiments, the dyskinesia is levodopa-induced dyskinesia (LID). In some embodiments, the dyskinesia is diphasic dyskinesia or peak-dose dyskinesia. In some embodiments, the dystonia is generalized dystonia, focal dystonia, segmental dystonia, or acute dystonia. In some embodiments, the akathisia is acute akathisia, chronic akathisia, pseudoakathisia, or withdrawal or "rebound" akathisia. In some embodiments, Trapidil N,N-diethyl-5-methyl-[1,2,4]triazolo[1,5-a]pyrimidin-7-amine. In some embodiments, the derivative comprises AR 12455, AR 12456, AR 12460, AR 12463, AR 12464, AR 12465, AR 12560, or AR 12565. In some embodiments, the metabolite comprises desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyt hyl)]amino-s-triazolo[1,5-a]pyrimidine, hydroxy- or ketopentyl derivatives, piperidinoles or piperidinones, TP1, or TP2. In some embodiments, the pharmaceutically acceptable salt comprises salts with hydrochloric acid, hydrobromic acid, hydroiodic acid, sulfuric acid, nitric acid, ocalic acid, malonic acid, or tartaric acid. In some embodiments, the additional therapeutic agent comprises clonazepam, Ginkgo biloba, clozapine, risperidone, quetiapine, vitamin E, levodopa, benzodiazepines, botulinum toxin, reserpine, tetrabenazine, propranolol, dopamine-depleting agents, ondansetron, zotepine, aripiprazole, zopiclone, zonisamide, trihexyphenidyl (Broflex), biperiden, procyclidine, diazepam, baclofen, tizanidine, carbamazepine, gabapentin, lorazepam, mianserin, cyproheptadine, mirtazapine, benztropin, trihexyphenidyl, carbidopa, ropinirole, pramipexole, bromocriptine, selegiline, rasagiline, ziprasidone, olanzapine, amantadine, valbenazine, dutetrabenazine, or diphenhydramine. In some embodiments, Trapidil, a derivative, a metabolite, a prodrug, an analog, or a pharmaceutically acceptable salt thereof is administered orally. In some embodiments, Trapidil, a derivative, a metabolite, a prodrug, an analog, or a pharmaceutically acceptable salt thereof is administered intravenously or subcutaneously. In some embodiments, the additional therapeutic agent is administered orally. In some embodiments, the additional therapeutic agent is administered intravenously or subcutaneously. In some embodiments, Trapidil, a derivative, a metabolite, a prodrug, an analog, or a pharmaceutically acceptable salt thereof and the additional therapeutic agent are administered simultaneously. In some embodiments, Trapidil, a derivative, a metabolite, a prodrug, an analog, or a pharmaceutically acceptable salt thereof and the additional therapeutic agent are administered sequentially. In some embodiments, Trapidil, a derivative, a metabolite, a prodrug, an analog, or a pharmaceutically acceptable salt thereof is administered before the administration of the additional therapeutic agent. In some embodiments, Trapidil, a derivative, a metabolite, a prodrug, an analog, or a pharmaceutically acceptable salt thereof is administered after the administration of the additional therapeutic agent. In some embodiments, Trapidil, a derivative, a metabolite, a prodrug, an analog, or a pharmaceutically acceptable salt thereof and the additional therapeutic agent are administered in a unified dosage form. In some embodiments, Trapidil, a derivative, a metabolite, a prodrug, an analog, or a pharmaceutically acceptable salt thereof and the additional therapeutic agent are administered in separate dosage forms. In some embodiments, the subject is diagnosed with an extrapyramidal syndrome. In some embodiments, the subject exhibits at least one marker that is associated with an extrapyramidal syndrome. In some embodiments, the subject is a human.

Disclosed herein, in certain embodiments, is a kit comprising a therapeutic effective dose of Trapidil, a derivative, a metabolite, a prodrug, an analog, or a pharmaceutically acceptable salt thereof, and an additional therapeutic agent.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
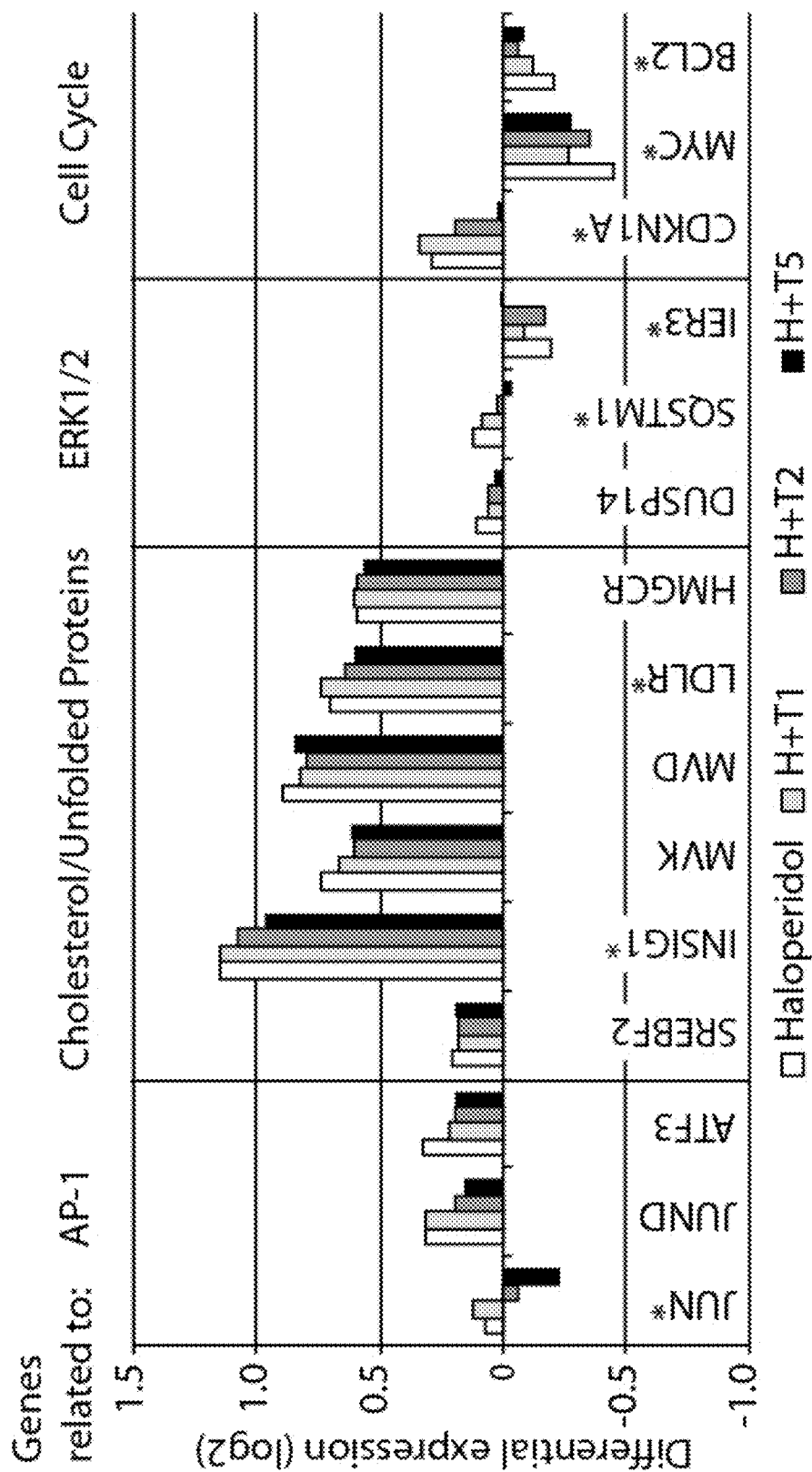
FIG. 1 shows Trapidil's ability to ameliorate or reverse the expression changes in key genes related to extrapyramidal syndromes induced by haloperidol, a potent first generation antipsychotic. * indicates that the change induced by Trapidil was significant at FDR <0.05.

Drugs are administered for treating pathologies and alleviating symptoms. Adverse drug reactions (ADRs) are negative side effects of drugs. In some instances, ADRs are classified into six types: 1) dose-related, 2) non-dose-related, 3) dose-related and time-related, 4) time-related, 5) withdrawal, and 6) failure of therapy. In some cases, ADRs cause a clinical and economic burden. According to the Food and Drug Administration (FDA) Adverse Event Reporting Systems, there are 100,000 deaths annually due to ADRs in the United States. For instances, ADRs are responsible for about 6.5% of hospital admissions. Further, ADRs and drug safety account for about 28% of Phase 2 and Phase 3 clinical trial failures. In some instances, ADRs are also responsible for drug withdrawals, for example, withdrawal of Vioxx by Merck and Co. and Lipobay by Bayer A.G. Additional management of ADRs includes, for example, alteration of the dosage regimen or specific treatment of its effects.

Extrapyramidal syndrome, disorders, symptoms or side effects are a particular set of ADRs that are drug-induced movement disorders. Depending on the drug used, extrapyramidal syndromes effect up to about 30-40% of patients taking the medication. In some instances, extrapyramidal syndromes further affect patient quality of life, leading to therapeutic non-compliance, and in rare cases lead to death.

In some instances, computational analysis correlates extrapyramidal syndromes or drug-induced movement disorders with an increase in ERK pathway (also known as MAPK pathway or Ras-Raf-MEK-ERK pathway) activity. For example, the analysis shows an increase in the expression of genes that are regulated by or interact with JUN, FOS, UBC, SREBF1, CEBPB, and/or MYC protein. In some instances, these proteins are directly upregulated by ERK signaling proteins. In addition, inflammatory markers such as IL-6, IL-12, and TNF-α are detected by the computational analysis. Furthermore, an increase in ERK activity and inflammation has been observed in levodopa-induced dyskinesia and in tardive dyskinesia. For example, upregulation of FOS and FOS-related proteins (FRA), which are regulated by ERK/MAPK, have been linked to levodopa-induced dyskinesia (Thanvi, et al., "Levodopa-induced dyskinesia in Parkinson's disease: clinical features, pathogenesis, prevention and treatment," *Postgrad Med J.* 83(980): 384-388 (2007)).

In some instances, Trapidil is shown in a computational analysis to modulate expression (e.g., gene expression) of JUN, UBC, and/or ERK signaling proteins. In some cases, Trapidil has also been correlated with a decrease in expression of genes that interact with inflammatory markers, such as TNF-α, IL-1a, and/or IL-1b, in which IL-1b has been shown to be linked to levodopa-induced dyskinesia.

Disclosed herein, in certain embodiments, are methods of treating an ADR in a subject in need thereof. In some instances, the ADR is an extrapyramidal syndrome. In some instances, disclosed herein is a method of treating an extrapyramidal syndrome in a subject in need thereof comprising administering to the subject a therapeutic effective dose of Trapidil, a derivative, a metabolite, a prodrug, an analog, or a pharmaceutically acceptable salt thereof.

Disclosed herein, in certain embodiments, is a method of preventing an extrapyramidal syndrome in a subject in need thereof comprising administering to the subject a therapeutic effective dose of Trapidil, a derivative, a metabolite, a prodrug, an analog, or a pharmaceutically acceptable salt thereof.

Disclosed herein, in certain embodiments, is a pharmaceutical combination which comprises a therapeutic effective dose of Trapidil, a derivative, a metabolite, a prodrug, an analog, or a pharmaceutically acceptable salt thereof; and an additional therapeutic agent.

Disclosed herein, in certain embodiments, include a dosage combination for use in a treatment of an extrapyramidal syndrome in a subject in need thereof, which comprises administering to the subject a therapeutic effective dose of Trapidil, a derivative, a metabolite, a prodrug, an analog, or a pharmaceutically acceptable salt thereof; and an additional therapeutic agent; wherein the therapeutic amount treats the extrapyramidal syndrome in the subject in need thereof.

Disclosed herein, in certain embodiments, is a kit which comprises a therapeutic effective dose of Trapidil, a derivative, a metabolite, a prodrug, an analog, or a pharmaceutically acceptable salt thereof; and an additional therapeutic agent.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed.

In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that is expected to be within experimental error.

The section headings used herein are for organizational purposes only and are not to be construed as limiting the subject matter described.

As used herein, "drug", "pharmaceutical", "small-molecule drug", "biologic drug", "biopharmaceutical", and "therapeutic", are used interchangeably to refer to an exogenous compound administered to a patient for a therapeutic purpose that do or do not have an adverse drug reaction (ADR). These compounds are obtained by the patient either with a prescription from a medical professional or without a prescription for over the counter items.

As used herein, "adverse drug reaction", "ADR", "adverse drug event", "adverse event", and "side effect" are used interchangeably to refer to an unintended and injurious consequence of a drug. In some instances, ADR is a single disease, symptom, sign, or diagnosis. For example, nausea is an ADR. In some instances, ADR is a single set of closely related diseases, symptoms, signs, or diagnoses. For example, the set of nausea and vomiting is an ADR.

As used herein, a "derivative" refers to compounds that are derived from or obtained from a compound disclosed herein. In some instances, a derivative improves its solubility, absorption, biological half-life, and the like, or decreases the toxicity of the molecule, eliminate or attenuate any undesirable side effect of the molecule, and the like.

In some instances, a derivative of a compound described herein include an isotopically labeled compound (e.g., with a radioisotope) or by another means, including, but not limited to, the use of chromophores or fluorescent moieties, bioluminescent labels, or chemiluminescent labels. Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that are incorporated into the present compounds include isotopes of hydrogen, carbon, nitrogen, oxygen, fluorine and chlorine, such as, for example, $^2H$, $^3H$, $^{13}C$, 14C, $^{15}N$, $^{18}O$, $^{17}O$, $^{35}S$, $^{18}F$, $^{36}Cl$. In some instances, isotopically-labeled compounds described herein, for example those into which radioactive isotopes such as 3H and $^{14}C$ are incorporated, are useful in drug and/or substrate tissue distribution assays.

In some embodiments, a derivative of a compound described herein is a deuterated version of the compound. In some instances, a deuterated version of the compound comprises at least one, two, three, four, five, six, seven, eight, nine, ten, or more deuterium substitutions. In some cases, substitution with isotopes such as deuterium affords certain therapeutic advantages resulting from greater metabolic stability, such as, for example, increased in vivo half-life or reduced dosage requirements.

In some instances, a derivative of a compound described herein comprises any of the following compounds:

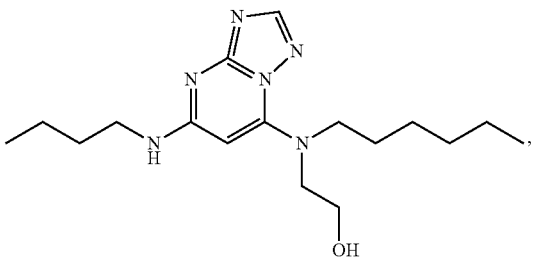
(AR 12455)

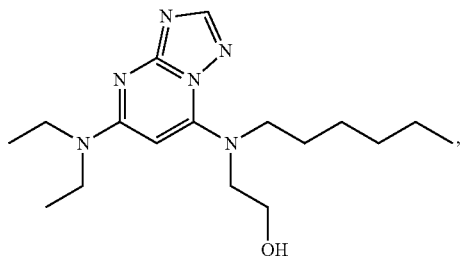
(AR12456)

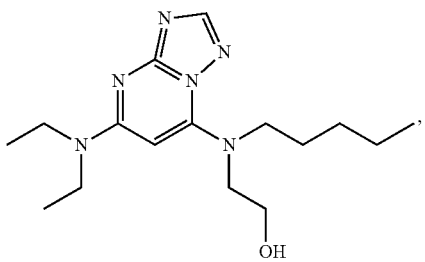
(AR12460)

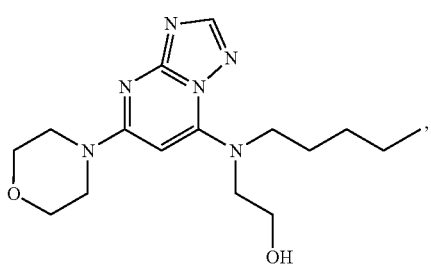
(AR 12463)

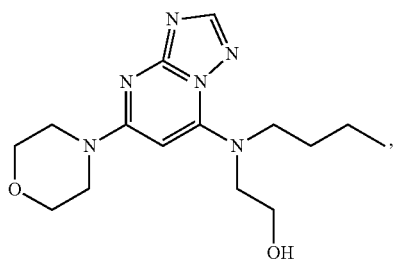
(AR 12464)

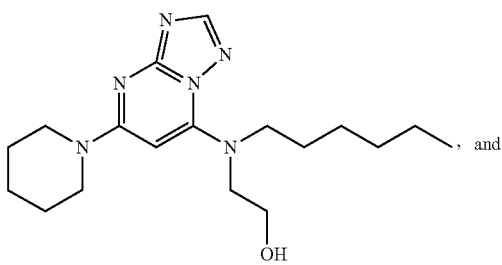
(AR 12465), and

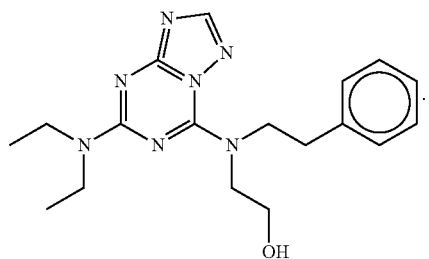
(AR 12565)

As used herein, a "metabolite" of a compound disclosed herein refers to the intermediates and products of that compound that is formed when the compound is metabolized. In additional embodiments, compounds described herein are metabolized upon administration to an organism in need to produce a metabolite that is then used to produce a desired effect, including a desired therapeutic effect. In some instances, a metabolite of a compound disclosed herein is an active metabolite. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, in some instances, enzymes produce specific structural alterations to a compound.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In some instances, exemplary metabolites disclosed herein include, but are not limited to, desethyl-trapidil, 5-piperidin-4'-olyl-7-[N-pentyl-N-(beta-hydroxyethyl)] amino-s-triazolo[1,5-a]pyrimidine, 5-piperidin-4'-olyl-7-[N-pent-4-olyl-N-(beta-hydroxyet hyl)]amino-s-triazolo[1, 5-a]pyrimidine, hydroxy- or ketopentyl derivatives, piperidinoles or piperidinones, TP1, or TP2.

In some embodiments, metabolites of the compounds disclosed herein are optionally identified either by administration of compounds to a host and analysis of tissue samples from the host, or by incubation of compounds with hepatic cells in vitro and analysis of the resulting compounds.

As used herein, a "prodrug" of a compound disclosed herein refers to an agent that is converted into the compound disclosed herein in vivo. Prodrugs are often useful because, in some situations, they are easier to administer than the parent drug. In some instances, prodrugs are bioavailable by oral administration whereas the parent is not. In some instances, the prodrugs have improved solubility in pharmaceutical compositions over the parent drug. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In some instances, the prodrug is designed to alter the metabolic stability or the transport characteristics of a drug, to mask side effects or toxicity, to improve the flavor of a drug or to alter other characteristics or properties of a drug. In some instances, prodrugs are designed as reversible drug derivatives, for use as modifiers to enhance drug transport to site-specific tissues. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985).

As used herein, an "analog" refers to compounds that are structurally and functionally similar to, or mimics the effects of, a compound disclosed herein. In some instances, an analog mimics the biological effect of a compound disclosed herein. In other instances, an analog mimics the physical effect of a compound disclosed herein.

As used herein, a "pharmaceutically acceptable salt" refer to salts of the compound disclosed herein that have no persistent detrimental effect on the general health of the subject being treated or does not abrogate the biological activity or properties of the compound, and is relatively non-toxic. In some embodiments, a "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds described herein, as well as active metabolites of these compounds having the same type of activity.

As used herein, the terms "individual(s)," "subject(s)," and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Extrapyramidal Syndrome

Extrapyramidal syndrome comprises a class of motor disorders induced by drugs. In some embodiments, the drug classes that have been identified to induce extrapyramidal syndrome include, but are not limited to: 1) antipsychotics, 2) levodopa, 3) antidepressants, 4) anti-cholinergics, which are used for example for respiratory problems, bladder control problems, or Parkinson's disease, 5) antiemetics, 6) anxiolytics for example for anxiety disorders, 7) antiepileptics, 8) anti-Parkinson's agents, 9) anti-malarials, and 10) antihistamines.

In some embodiments, extrapyramidal syndromes, symptoms, disorders, or side effects include: Movement disorder, Dyskinesia, Akathisia, Tardive Dyskinesia, Psychomotor hyperactivity, Abnormal involuntary movements, Acute dyskinesia, Jerkiness, Jerky movements, Mouth movement impaired, Oral dyskinesia, Tongue protrusions, Facial jerks, Shuddering attacks, Motor restlessness, Motor unrest compulsive, levodopa-induced dyskinesia, neuroleptic-induced dyskinesia, Dystonias, Drug-induced Parkinsonism, Pseudo Parkinsonism, Bradykinesia, Tremors, Rigidity, and Lip smacking.

In some embodiments, disclosed herein is a method of treating an extrapyramidal syndrome induced by an antipsychotic, levodopa, an antidepressant, an anti-cholinergic, an antiemetic, an anxiolytic, an antiepileptic, an anti-Parkinson's agent, an anti-malarial, or an antihistamine, in a subject in need thereof comprising administering to the subject a therapeutic effective dose of Trapidil, a derivative, a metabolite, a prodrug, an analog, or a pharmaceutically acceptable salt thereof. In additional embodiments, disclosed herein is a method of treating a subject exhibiting one or more of an extrapyramidal symptoms such as movement disorder, dyskinesia, akathisia, tardive dyskinesia, psychomotor hyperactivity, abnormal involuntary movements, acute dyskinesia, jerkiness, jerky movements, mouth movement impaired, oral dyskinesia, tongue protrusions, facial jerks, shuddering attacks, motor restlessness, motor unrest compulsive, levodopa-induced dyskinesia, neuroleptic-induced dyskinesia, dystonias, drug-induced parkinsonism, pseudo parkinsonism, bradykinesia, tremors, rigidity, and lip smacking with a therapeutic effective dose of Trapidil, a derivative, a metabolite, a prodrug, an analog, or a pharmaceutically acceptable salt thereof.

Dyskinesia

In some embodiments, the extrapyramidal syndrome is dyskinesia. In some embodiments, dyskinesia is tardive dyskinesia (TD), levodopa-induced dyskinesia (LID), diphasic dyskinesia, or peak-dose dyskinesia. In some embodiments, dyskinesia is tardive dyskinesia (TD). In some embodiments, dyskinesia is levodopa-induced dyskinesia (LID). In some embodiments, dyskinesia is diphasic dyskinesia. In some embodiments, dyskinesia is peak-dose dyskinesia.

In some embodiments, dyskinesia is an extrapyramidal syndrome that is drug-induced movement disorder. Dyskinesia refers to a category of movement disorders that are characterized by involuntary muscle movements, including movements similar to tics or chorea and diminished voluntary movements. Dyskinesia includes for example, from a slight tremor of the hands to an uncontrollable movement of the upper body or lower extremities. Dyskinesia is a symptom of several medical disorders that are distinguished by their underlying cause.

In some embodiments, dyskinesia is tardive dyskinesia (TD). Tardive dyskinesia refers to a type of dyskinesia resulting in repetitive, involuntary, purposeless body movements comprising but not limited to grimacing, tongue movements, lip smacking, lip puckering, pursing of the lips, or excessive eye blinking. The involuntary movements have slow or belated onset. In some embodiments, this syndrome occurs as a result of long-term or high-dose use of antipsychotic drugs, or in children and infants as a side effect from usage of drugs for gastrointestinal disorders. In some instances, TD is caused by antipsychotic, levodopa, antidepressants, anti-cholinergics, antiemetics, antiepileptics, antimalarials, and antihistamines.

In some embodiments, dyskinesia is levodopa-induced dyskinesia (LID). Levodopa-induced dyskinesia refers to a form of dyskinesia associated with levodopa which is used in the treatment for the motor symptoms of Parkinson's disease. LID often involves hyperkinetic movements, including chorea, dystonia, and athetosis.

In some embodiments, dyskinesia is diphasic dyskinesia. Diphasic dyskinesia refers to a type of levodopa-induced dyskinesia that develop when plasma levodopa levels are rising or falling, but not with the peak levels. Diphasic dyskinesia primarily occurs in the lower limbs and is often dystonic or ballistic. This form of dyskinesia does not respond to reductions in the dosage of levodopa.

In some embodiments, dyskinesia is peak-dose dyskinesia. Peak-dose dyskinesia refers to a form of levodopa-induced dyskinesia that correlates with the peak plasma levels of levodopa. Peak-dose dyskinesia involves the head, truck, and limbs, and sometimes respiratory muscles. Peak-dose dyskinesia responds to reductions in the dosage of levodopa but at the cost of deterioration of Parkinsonism.

In some embodiments, disclosed herein is a method of treating dyskinesia with administration of a therapeutic effective dose of Trapidil, a derivative, a metabolite, a prodrug, an analog, or a pharmaceutically acceptable salt thereof. In some embodiments, dyskinesia is tardive dyskinesia (TD), levodopa-induced dyskinesia (LID), diphasic dyskinesia, or peak-dose dyskinesia. In some cases, disclosed herein is a method of treating tardive dyskinesia (TD) with administration of a therapeutic effective dose of Trapidil, a derivative, a metabolite, a prodrug, an analog, or a pharmaceutically acceptable salt thereof. In some cases, disclosed herein is a method of treating levodopa-induced dyskinesia (LID) with administration of a therapeutic effective dose of Trapidil, a derivative, a metabolite, a prodrug, an analog, or a pharmaceutically acceptable salt thereof. In some cases, disclosed herein is a method of treating diphasic dyskinesia with administration of a therapeutic effective dose of Trapidil, a derivative, a metabolite, a prodrug, an analog, or a pharmaceutically acceptable salt thereof. In some cases, disclosed herein is a method of treating peak-dose dyskinesia with administration of a therapeutic effective dose of Trapidil, a derivative, a metabolite, a prodrug, an analog, or a pharmaceutically acceptable salt thereof.

Dystonia

In some embodiments, the extrapyramidal syndrome is dystonia. In some embodiments, dystonia is generalized dystonia, focal dystonia, segmental dystonia, or acute dystonia. In some embodiments, dystonia is generalized dystonia. In some embodiments, dystonia is focal dystonia. In some embodiments, dystonia is segmental dystonia. In some embodiments, dystonia is acute dystonia.

In some embodiments, the extrapyramidal syndrome is dystonia. Dystonia refers to a movement disorder in which sustained muscle contractions cause twisting and repetitive movements or abnormal postures. In some instances, the movements resemble tremors. Dystonia is often initiated or worsened by voluntary movements, and symptoms "overflow" into adjacent muscles. In some embodiments, dystonia is drug-induced dystonia. Dystonic reactions are characterized by intermittent spasmodic or sustained involuntary contractions of the muscles in the face, neck, trunk, pelvis, extremities, and larynx.

In some embodiments, dystonia is generalized dystonia. Generalized dystonia refers to a form of dystonia that affects most or all of the body.

In some embodiments, dystonia is focal dystonia. Focal dystonia refers to a form of dystonia that is localized to a specific part of the body. In some instances, focal dystonia is multifocal dystonia which involves two or more unrelated body parts.

In some embodiments, dystonia is segmental dystonia. Segmental dystonia refers to a form of dystonia that affects two or more adjacent parts of the body.

In some embodiments, dystonia is acute dystonia. Acute dystonia refers to a form of dystonia consisting of sustained, often painful muscular spasms, producing twisting abnormal postures.

In some embodiments, disclosed herein is a method of treating dystonia with administration of a therapeutic effective dose of Trapidil, a derivative, a metabolite, a prodrug, an analog, or a pharmaceutically acceptable salt thereof. In some embodiments, dystonia is generalized dystonia, focal dystonia, segmental dystonia, or acute dystonia. In some cases, disclosed herein is a method of treating generalized dystonia with administration of a therapeutic effective dose of Trapidil, a derivative, a metabolite, a prodrug, an analog, or a pharmaceutically acceptable salt thereof. In some cases, disclosed herein is a method of treating focal dystonia with administration of a therapeutic effective dose of Trapidil, a derivative, a metabolite, a prodrug, an analog, or a pharmaceutically acceptable salt thereof. In some cases, disclosed herein is a method of treating segmental dystonia with administration of a therapeutic effective dose of Trapidil, a derivative, a metabolite, a prodrug, an analog, or a pharmaceutically acceptable salt thereof. In some cases, disclosed herein is a method of treating acute dystonia with administration of a therapeutic effective dose of Trapidil, a derivative, a metabolite, a prodrug, an analog, or a pharmaceutically acceptable salt thereof.

Akathisia

In some embodiments, as disclosed herein, the extrapyramidal syndrome is akathisia. In some embodiments, akathisia is acute akathisia, chronic akathisia, pseudoakathisia, or withdrawal or "rebound" akathisia. In some embodiments, akathisia is acute akathisia. In some embodiments, akathisia is chronic akathisia. In some embodiments, akathisia is pseudoakathisia. In some embodiments, akathisia is withdrawal or "rebound" akathisia.

In some embodiments the extrapyramidal syndrome is akathisia. In some embodiments, akathisia is a movement disorder characterized by a feeling of inner restlessness and a compelling need to be in constant motion, as well as by actions such as rocking while standing or sitting, lifting the feet as if marching on the spot, and crossing and uncrossing the legs while sitting. In some embodiments, akathisia is drug-induced.

In some embodiments, akathisia is acute akathisia. Acute akathisia refers to a form of akathisia that develops soon after 1) starting medication or following dose increase, 2) switching to a high-potency drug, or 3) withdrawal of a medication. In some instances, duration of acute akathisia is less than six months and includes intense dysphoria, awareness of restlessness and complex and semi-purposeful motor fidgetiness.

In some embodiments, akathisia is chronic akathisia. Chronic akathisia refers to a form of akathisia that persists for over six months after last dosage increment of the drug. In some instances, chronic akathisia includes mild dysphoria, awareness of restlessness, motor fidgetiness with stereotypes movement and limb and orofacial dyskinesia.

In some embodiments, akathisia is pseudoakathisia. In some instances, pseudoakathisia is late stage of chronic akathisia. Exemplary symptoms include motor manifestations with subjective component, motor fidgetiness with stereotyped movement and limb and orofacial dyskinesia.

In some embodiments, akathisia is withdrawal or "rebound" akathisia. In some instances, withdrawal or "rebound" akathisia refers to akathisia associated with switching drugs with an onset of usually within six weeks of discontinuation or dose decrease of the drug.

In some embodiments, disclosed herein is a method of treating akathisia with administration of a therapeutic effective dose of Trapidil, a derivative, a metabolite, a prodrug, an analog, or a pharmaceutically acceptable salt thereof. In some embodiments, akathisia is acute akathisia, chronic akathisia, pseudoakathisia, or withdrawal or "rebound" akathisia. In some cases, disclosed herein is a method of treating acute akathisia with administration of a therapeutic effective dose of Trapidil, a derivative, a metabolite, a prodrug, an analog, or a pharmaceutically acceptable salt thereof. In some cases, disclosed herein is a method of treating chronic akathisia with administration of a therapeutic effective dose of Trapidil, a derivative, a metabolite, a prodrug, an analog, or a pharmaceutically acceptable salt thereof. In some cases, disclosed herein is a method of treating pseudoakathisia with administration of a therapeutic effective dose of Trapidil, a derivative, a metabolite, a prodrug, an analog, or a pharmaceutically acceptable salt thereof. In some cases, disclosed herein is a method of treating withdrawal or "rebound" akathisia with administration of a therapeutic effective dose of Trapidil, a derivative, a metabolite, a prodrug, an analog, or a pharmaceutically acceptable salt thereof.

Drug-Induced Parkinsonism

In some embodiments, as disclosed herein, the extrapyramidal syndrome is drug-induced Parkinsonism. In some instances, drug-induced Parkinsonism is a movement disorder characterized by rigidity, bradykinesia, tremor, masked facies, shuffling gait, stooped posture, sialorrhoea and seborrhea. In some embodiments, disclosed herein is a method of treating drug-induced Parkinsonism with administration of a therapeutic effective dose of Trapidil, a derivative, a metabolite, a prodrug, an analog, or a pharmaceutically acceptable salt thereof.

Extrapyramidal Syndrome Transcriptomic Signature

In some embodiments, disclosed herein, are a panel of markers that are associated with an extrapyramidal syndrome. In some embodiments, the panel comprises markers that are associated with activator protein-1 (AP-1), cholesterol synthesis and unfolded protein response, ERK signaling, and cell cycle progression. In some instances, markers that are associated with AP-1 comprise FOSL2, JUN, JUND, and ATF3. In some instances, markers that are associated with cholesterol synthesis and unfolded protein response comprise SREBF2, INSIG1, MVK, MVD, LDLR, and HMGCR. In some cases, markers that are associated with ERK signaling comprise DUSP14, SQSTM1, and IER3. In some cases, markers that are associated with cell cycle comprise CDKN1A, MYC, and BCL2. In some embodiments, the panel of markers that are associated with an extrapyramidal syndrome comprise FOSL2, JUN, JUND, ATF3, SREBF2, INSIG1, MVK, MVD, LDLR, HMGCR, ERK, DUSP14, SQSTM1, IER3, CDKN1A, MYC, and BCL2. In some embodiments, the panel that are associated with an extrapyramidal syndrome comprises markers JUN, JUND, ATF3, SREBF2, INSIG1, MVK, MVD, LDLR, HMGCR, DUSP14, SQSTM1, IER3, CDKN1A, MYC, and BCL2. In some embodiments, the panel that are associated with an extrapyramidal syndrome comprises markers FOSL2, JUN, JUND, ATF3, SREBF2, INSIG1, MVK, MVD, LDLR, HMGCR, SQSTM1, IER3, CDKN1A, MYC, and BCL2. In some instances, the panel that are associated with an extrapyramidal syndrome comprises FOSL2, JUN, SREBF1, CEBPB, UBC, and ERK. In some cases, the panel that are associated with an extrapyramidal syndrome comprises MYC and BCL2.

In some instances, computational analysis correlates extrapyramidal syndromes or drug-induced movement disorders with a transcriptome signature of the drugs that cause extrapyramidal syndromes or drug-induced movement disorders. In some instances, computational analysis correlates extrapyramidal syndromes or drug-induced movement disorders with an increase in ERK signaling activity. In some instances, computational analysis correlates extrapyramidal syndromes or drug-induced movement disorders with an upregulation of the transcription of transcription factors and proteins related to activator protein-1. In some instances, computational analysis correlates extrapyramidal syndromes or drug-induced movement disorders with an upregulation of FOS. In some instances, computational analysis correlates extrapyramidal syndromes or drug-induced movement disorders with an upregulation of JUN. In some instances, computational analysis correlates extrapyramidal syndromes or drug-induced movement disorders with an upregulation of JUND. In some instances, computational analysis correlates extrapyramidal syndromes or drug-induced movement disorders with an upregulation of ATF3. In some instances, computational analysis correlates extrapyramidal syndromes or drug-induced movement disorders with an upregulation in transcription factors and proteins related to cholesterol synthesis and unfolded protein response. In some instances, computational analysis correlates extrapyramidal syndromes or drug-induced movement disorders with an upregulation of SREBF1. In some instances, computational analysis correlates extrapyramidal syndromes or drug-induced movement disorders with an upregulation of CEBPB. In some instances, computational analysis correlates extrapyramidal syndromes or drug-induced movement disorders with an upregulation of UBC. In some instances, computational analysis correlates extrapyramidal syndromes or drug-induced movement disorders with an upregulation of INSIG1. In some instances, computational analysis correlates extrapyramidal syndromes or drug-induced movement disorders with an upregulation of MVK. In some instances, computational analysis correlates extrapyramidal syndromes or drug-induced movement disorders with an upregulation of MVD. In some instances, computational analysis correlates extrapyramidal syndromes or drug-induced movement disorders with an upregulation of LDLR. In some instances, computational analysis correlates extrapyramidal syndromes or drug-induced movement disorders with an upregulation of HMGCR. In some instances, computational analysis correlates extrapyramidal syndromes or drug-induced movement disorders with an upregulation of ERK (e.g., ERK1, ERK2). In some instances, computational analysis correlates extrapyramidal syndromes or drug-induced movement disorders with a downregulation in transcription factors and proteins related to cell cycle progression. In some instances, computational analysis correlates extrapyramidal syndromes or drug-induced movement disorders with a downregulation of MYC. In some instances, computational analysis correlates extrapyramidal syndromes or drug-induced movement disorders with a downregulation of BCL2.

In some embodiments, computational analysis correlates extrapyramidal syndromes or drug-induced movement disorders with a compound that reverses the transcriptomic signature. In some instances, the compound is Trapidil, a derivative, a metabolite, or a pharmaceutically acceptable salt thereof.

In some embodiments, administration of a therapeutic effective dose of Trapidil, a derivative, a metabolite, or a pharmaceutically acceptable salt thereof modulate the expression of FOSL2, JUN, JUND, ATF3, SREBF2, INSIG1, MVK, MVD, LDLR, HMGCR, ERK, DUSP14, SQSTM1, IER3, CDKN1A, MYC, and BCL2. In some instances, administration of a therapeutic effective dose of Trapidil, a derivative, a metabolite, or a pharmaceutically acceptable salt thereof downregulates FOSL2, JUN, SREBF1, CEBPB, UBC, ERK, or a combination thereof. In additional instances, administration of a therapeutic effective dose of Trapidil, a derivative, a metabolite, or a pharmaceutically acceptable salt thereof upregulates MYC, BCL2, or a combination thereof. In some embodiments, also disclosed herein is a method of monitoring the treatment regimen in a subject administered with a therapeutic effective dose of Trapidil, a derivative, a metabolite, or a pharmaceutically acceptable salt thereof. In some instances, the method comprises administering to the subject a therapeutic effective dose of Trapidil, a derivative, a metabolite, or a pharmaceutically acceptable salt thereof, determining the expression of a marker selected from the panel of markers: FOSL2, JUN, JUND, ATF3, SREBF2, INSIG1, MVK, MVD, LDLR, HMGCR, ERK, DUSP14, SQSTM1, IER3, CDKN1A, MYC, and BCL2, and based on the expression level of the marker, continuing or discontinuing the treatment. In some cases, the method comprises contacting at least one gene selected from the panel: FOSL2, JUN, JUND, ATF3, SREBF2, INSIG1, MVK, MVD, LDLR, HMGCR, ERK, DUSP14, SQSTM1, IER3, CDKN1A, MYC, and BCL2 with a set of primers to produce amplified nucleic acids, wherein the at least one gene is isolated from a sample obtained from the subject after treatment initiation, and determining the level of the amplified nucleic acids in the sample relative to a control. In some cases, if the expression level of FOSL2, JUN, SREBF1, CEBPB, UBC, ERK, or a combination thereof is downregulated relative to a control, the treatment dosage is optionally decreased or discontinued. In some cases, if the expression level of MYC, BCL2, or a combination thereof is upregulated relative to a control, the treatment dosage is optionally decreased or discontinued. In some cases, a protein expression level instead of a nucleic acid level is determined. In some cases, the control is the expression level of the panel of markers from a normal sample or from a sample obtained from a subject not suffering from an extrapyramidal syndrome.

In some embodiments, also disclosed herein is a method of selecting a subject for treatment based on the expression level of a marker from the panel of markers: FOSL2, JUN, JUND, ATF3, SREBF2, INSIG1, MVK, MVD, LDLR, HMGCR, ERK, DUSP14, SQSTM1, IER3, CDKN1A, MYC, and BCL2. In some instances, a subject with an elevated expression level of FOSL2, JUN, SREBF1, CEBPB, UBC, ERK, or a combination thereof relative to the expression level from a control; and/or a decreased expression level of MYC, BCL2, or a combination thereof relative to the expression level from a control are treated with a therapeutic effective dose of Trapidil, a derivative, a metabolite, or a pharmaceutically acceptable salt thereof. In some cases, the expression level is a nucleic acid level. In other cases, the expression level is a protein expression level. In some instances, the control is the expression level of the panel of markers from a normal sample or from a sample obtained from a subject not suffering from an extrapyramidal syndrome.

Activator Protein-1 (AP-11)

AP-1 (activator protein-1) is a dimeric transcription factor comprising Jun, Fos or ATF (activating transcription factor) subunits that bind to a common DNA site, the AP-1-binding site, and is involved in cellular proliferation, differentiation, and apoptosis.

FOS

The Fos gene family comprises 4 members: FOS, FOSB, FOSL1, and FOSL2. These genes encode leucine zipper proteins that dimerize with proteins of the JUN family, thereby forming the transcription factor complex AP-1. In some instances, FOS proteins are regulators of cell proliferation, differentiation, and transformation. In some cases, expression of the FOS gene is associated with apoptotic cell death.

JUN

JUN is a protein that with Fos forms the AP-1 transcription factor. It is activated through double phosphorylation by the JNK pathway.

JUND

JUND, or JunD Proto-Oncogene, is an intronless gene that encodes a protein that is a member of the JUN family, and a functional component of the AP1 transcription factor complex.

ATF3

ATF3, or Activating Transcription Factor 3, encodes a member of the mammalian activation transcription factor/cAMP responsive element-binding (CREB) protein family of transcription factors. ATF3 represses transcription from promoters with ATF sites.

Cholesterol Synthesis and Unfolded Protein Response

Cholesterol is an important biological molecule that has roles in membrane structure as well as being a precursor for the synthesis of the steroid hormones, the bile acids, and vitamin D.

SREBF1

SREBF1, or Sterol Regulatory Element Binding Transcription Factor 1, encodes a transcription factor that binds to the sterol regulatory element-1 (SRE1), which is a decamer flanking the low density lipoprotein receptor gene and some genes involved in sterol biosynthesis. The protein is a member of the basic helix-loop-helix-leucine zipper (bHLH-Zip) transcription factor family.

SREBF2

SREBF2, or Sterol Regulatory Element Binding Transcription Factor 2, encodes a ubiquitously expressed transcription factor that controls cholesterol homeostasis by regulating transcription of sterol-regulated genes. The encoded protein contains a basic helix-loop-helix-leucine zipper (bHLH-Zip) domain and binds the sterol regulatory element 1 motif.

CEBPB

CEBPB is an intronless gene that encodes a transcription factor that contains a basic leucine zipper (bZIP) domain. The encoded protein functions as a homodimer but in some instances, also forms heterodimers with CCAAT/enhancer-binding proteins alpha, delta, and gamma. Activity of this protein is important in the regulation of genes involved in immune and inflammatory responses, among other processes.

UBC

UBC, or Ubiquitin C, encodes a polyubiquitin precursor protein. Ubiquitination is associated with protein degradation, DNA repair, cell cycle regulation, kinase modification, endocytosis, and regulation of other cell signaling pathways.

INSIG1

INSIG1, or Insulin Induced Gene 1, encodes an endoplasmic reticulum membrane protein that regulates cholesterol metabolism, lipogenesis, and glucose homeostasis. It mediates feedback control of cholesterol synthesis by controlling SCAP and HMGCR and functions by blocking the processing of sterol regulatory element-binding proteins (SREBPs).

MVK

MVK, or Mevalonate Kinase, encodes the peroxisomal enzyme mevalonate kinase. Mevalonate is a key intermediate, and mevalonate kinase is a key early enzyme in isoprenoid and sterol synthesis.

MVD

MVD, or Mevalonate Diphosphate Decarboxylase, catalyzes the conversion of mevalonate pyrophosphate into isopentenyl pyrophosphate in one of the early steps in cholesterol biosynthesis.

LDLR

LDLR, or Low Density Lipoprotein Receptor, gene family consists of cell surface proteins involved in receptor-mediated endocytosis of specific ligands. LDLR binds LDL, a major cholesterol-carrying lipoprotein of plasma, and transports it into cells by endocytosis.

HMGCR

HMGCR, or HMG-CoA Reductase, is the rate-limiting enzyme for cholesterol synthesis and is regulated via a negative feedback mechanism mediated by sterols and non-sterol metabolites derived from mevalonate, the product of the reaction catalyzed by reductase.

ERK Signaling

The ERK signaling cascade, defined by Extracellular Signal-regulated Kinase-1 (ERK1) and ERK2, plays a role in the regulation of various cellular processes such as proliferation, differentiation, development, learning, survival and, in some instances, also apoptosis.

DUSP14

DUSP14, or Dual Specificity Phosphatase 14, plays a role in the inactivation of MAP kinases and dephosphorylates ERK, JNK and p38 MAP-kinases.

SQSTM1

SQSTM1, or Sequestosome 1, encodes a multifunctional protein that binds ubiquitin and regulates activation of the nuclear factor kappa-B (NF-kB) signaling pathway. SQSTM1 plays a role in cell differentiation, apoptosis, immune response and in regulation of K(+) channels.

IER3

IER3, or Immediate Early Response 3, functions in the protection of cells from Fas- or tumor necrosis factor type alpha-induced apoptosis. In some instances, IER3 plays a role in the ERK signaling pathway by inhibiting the dephosphorylation of ERK by phosphatase PP2A-PPP2R5C holoenzyme. In some instances, IER3 acts as an ERK downstream effector mediating survival.

Cell Cycle

CDKN1A

CDKN1A, or Cyclin Dependent Kinase Inhibitor 1A, encodes a cyclin-dependent kinase inhibitor. The encoded protein binds to and inhibits the activity of cyclin-cyclin-dependent kinase2 or -cyclin-dependent kinase4 complexes, and thus functions as a regulator of cell cycle progression at G1. In some instances, CDKN1A interacts with proliferating cell nuclear antigen, a DNA polymerase accessory factor, and plays a regulatory role in S phase DNA replication and DNA damage repair.

MYC

MYC encodes a multifunctional, nuclear phosphoprotein that plays a role in cell cycle progression, apoptosis and cellular transformation. It functions as a transcription factor that regulates transcription of specific target genes.

BCL2

BCL2 encodes an integral outer mitochondrial membrane protein that blocks the apoptotic death of some cells such as lymphocytes and neural cells.

Trapidil

Trapidil, a triazolopyrimidine, belong to a class of anti-platelet drug. In some instances, Trapidil has been shown to decrease ERK activity. In some cases, Trapidil has been shown to exert anti-inflammatory properties, e.g., through reduced production of IL-6, IL-12, and TNF-α; and decreased activity NF-κB. Further, Trapidil has been observed to lower lipid peroxidation and to increase nitric oxide precursor availability, both, for example, have been implicated in tardive dyskinesia. In some embodiments, disclosed herein are methods and pharmaceutical combinations of treating an extrapyramidal syndrome in a subject in need thereof comprising administering to the subject a therapeutic effective dose of Trapidil. In other embodiments, disclosed herein are methods and pharmaceutical combinations of preventing an extrapyramidal syndrome in a subject in need thereof comprising administering to the subject a therapeutic effective dose of Trapidil. In additional embodiments, disclosed herein are methods and pharmaceutical combinations of treating or preventing an extrapyramidal syndrome in a subject in need thereof comprising administering to the subject a therapeutic effective dose of a derivative, a metabolite, a prodrug, an analog, or a pharmaceutically acceptable salt thereof of Trapidil.

Trapidil has the IUPAC name N,N-diethyl-5-methyl-[1,2,4]triazolo[1,5-a]pyrimidin-7-amine and the following chemical structure:

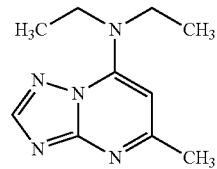

In some instances, Trapidil also has the names AR 12008, Avantrin, Trapymin, Trapymine, Trapidilum, Angichromen, Estelinol, Karnachol, Perucarate, Rocornal, Trapidil Towa Yakuhin, and Travisco. In additional instances, Trapidil is referred to herein as SB-0107.

Exemplary Trapidil derivatives include, but are not limited to, AR 12455, AR 12456, AR 12460, AR 12463, AR 12464, AR 12465, AR 12560, or AR 12565.

Exemplary Trapidil metabolites include, but are not limited to, desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyethyl)]amino-s-triazolo[1,5-a]pyrimidine, hydroxy- or keto-pentyl derivatives, piperidinoles or piperidinones, TP1, or TP2.

In some embodiments, exemplary pharmaceutically acceptable salts of Trapidil include, but are not limited to, salts with hydrochloric acid, hydrobromic acid, hydroiodic acid, sulfuric acid, nitric acid, ocalic acid, malonic acid, or tartaric acid.

In some embodiments, Trapidil is a Trapidil disclosed in U.S. Pat. No. 6,015,578; European Patent No. 0301423; or PCT Publication No. WO1993/009781.

In some embodiments, Trapidil is a Trapidil derivative disclosed in Heinroth-Hoffmann et al. (1990) "Influence of Trapidil and Trapidil Derivatives on the Content of Cyclic Nucleotides in Human Intima Cells Cultured from Atherosclerotic Plaques," *Drug Development Research*, 19(3), 321-327; Heinroth et al. (1983) "Influence of Trapidil derivatives on arachidonic acid- and prostaglandin endoperoxide analogue-induced platelet aggregation and thromboxane A2 formation," *Biomedica biochimica acta*, 43(8-9), S389-92; or Krause et al. (1985) *Advances in Pharmacological Research and Practice*: Proceedings of the 4th Congress of the Hungarian Pharmacological Society, Budapest, pages 139-142.

In some embodiments, Trapidil is a Trapidil metabolite disclosed in Thürmann et al. (1997) "Pharmacokinetics of the PDGF-antagonist Trapidil in patients with and without renal impairment," *Clinical nephrology*, 47(2), 99-105; or Pfeifer et al. (1990) "Biotransformation of the Trapidil (rocornal) derivative AR 12463 in the rat," *Die Pharmazie*, 45(8), 609-614.

In some embodiments, Trapidil is a Trapidil salt disclosed in U.S. Pat. No. 6,369,065.

In some embodiments, also disclosed herein is a method of treating a patient with an upregulated ERK pathway-associated protein with administration of a therapeutic effective dose of Trapidil, a derivative, a metabolite, a prodrug, an analog, or a pharmaceutically acceptable salt thereof. In some instances, the ERK pathway-associated protein comprises JUN, FOS, UBC, SREBF1, CEBPB, or MYC protein. In some embodiments, also disclosed herein is a method of treating a patient with an upregulated JUN, FOS, UBC, SREBF1, CEBPB, or MYC protein with administration of a therapeutic effective dose of Trapidil, a derivative, a metabolite, a prodrug, an analog, or a pharmaceutically acceptable salt thereof.

In some instances, disclosed herein is a method of treating a patient with an upregulated inflammatory marker with administration of a therapeutic effective dose of Trapidil, a derivative, a metabolite, a prodrug, an analog, or a pharmaceutically acceptable salt thereof. In some cases, the inflammatory marker comprises TNF-α, IL-1a, IL-1b, IL-6, IL-12, or NF-κB. In some instances, disclosed herein is a method of treating a patient with an upregulated inflammatory marker such as TNF-α, IL-1a, IL-1b, IL-6, IL-12, or NF-κB with administration of a therapeutic effective dose of Trapidil, a derivative, a metabolite, a prodrug, an analog, or a pharmaceutically acceptable salt thereof.

In some embodiments, Trapidil comprises Trapidil derivatives such as AR 12455, AR 12456, AR 12460, AR 12463, AR 12464, AR 12465, AR 12560, or AR 12565; Trapidil metabolites such as: desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyethyl)]amino-s-triazolo[1,5-a]pyrimidine, hydroxy- or ketopentyl derivatives, piperidinoles or piperidinones, TP1, or TP2; pharmaceutically acceptable salts of Trapidil such as: salts with hydrochloric acid, hydrobromic acid, hydroiodic acid, sulfuric acid, nitric acid, ocalic acid, malonic acid, or tartaric acid.

In some embodiments, Trapidil, a derivative, a metabolite, a prodrug, an analog, or a pharmaceutically acceptable salt thereof is administered at a dose range from about 10 mg per day to about 3000 mg per day. In some instances, the dose range is from about 10 mg per day to about 2900 mg per day, from about 10 mg per day to about 2800 mg per day, from about 10 mg per day to about 2700 mg per day, from about 10 mg per day to about 2600 mg per day, from about 10 mg per day to about 2500 mg per day, from about 10 mg per day to about 2400 mg per day, from about 10 mg per day to about 2300 mg per day, from about 10 mg per day to about 2200 mg per day, from about 10 mg per day to about 2100 mg per day, from about 10 mg per day to about 2000 mg per day, from about 10 mg per day to about 1900 mg per day, from about 10 mg per day to about 1800 mg per day, from about 10 mg per day to about 1700 mg per day, from about 10 mg per day to about 1600 mg per day, from about 10 mg per day to about 1500 mg per day, from about 10 mg per day to about 1400 mg per day, from about 10 mg per day to about 1300 mg per day, from about 10 mg per day to about 1200 mg per day, from about 10 mg per day to about 1100 mg per day, from about 10 mg per day to about 1000 mg per day, from about 10 mg per day to about 950 mg per day, from about 10 mg per day to about 900 mg per day, from about 10 mg per day to about 850 mg per day, from about 10 mg per day to about 800 mg per day, from about 10 mg per day to about 750 mg per day, from about 10 mg per day to about 700 mg per day, from about 10 mg per day to about 650 mg per day, from about 10 mg per day to about 600 mg per day, from about 10 mg per day to about 550 mg per day, from about 10 mg per day to about 500 mg per day, from about 10 mg per day to about 450 mg per day, from about 10 mg per day to about 400 mg per day, from about 10 mg per day to about 350 mg per day, from about 10 mg per day to about 300 mg per day, from about 10 mg per day to about 250 mg per day, from about 10 mg per day to about 200 mg per day, from about 10 mg per day to about 150 mg per day, from about 10 mg per day to about 100 mg per day, from about 50 mg per day to about 3000 mg per day, from about 100 mg per day to about 3000 mg per day, from about 150 mg per day to about 3000 mg per day, from about 200 mg per day to about 3000 mg per day, from about 300 mg per day to about 3000 mg per day, from about 400 mg per day to about 3000 mg per day, from about 500 mg per day to about 3000 mg per day, from about 600 mg per day to about 3000 mg per day, from about 700 mg per day to about 3000 mg per day, from about 800 mg per day to about 3000 mg per day, from about 900 mg per day to about 3000 mg per day, from about 1000 mg per day to about 3000 mg per day, from about 1100 mg per day to about 3000 mg per day, from about 1200 mg per day to about 3000 mg per day, from about 1300 mg per day to about 3000 mg per day, from about 1400 mg per day to about 3000 mg per day, from about 1500 mg per day to about 3000 mg per day, from about 1600 mg per day to about 3000 mg per day, from about 1700 mg per day to about 3000 mg per day, from about 1800 mg per day to about 3000 mg per day, from about 1900 mg per day to about 3000 mg per day, from about 2000 mg per day to about 3000 mg per day, from about 2100 mg per day to about 3000 mg per day, from about 2200 mg per day to about 3000 mg per day, from about 2300 mg per day to about 3000 mg per day, from about 2400 mg per day to about 3000 mg per day, from about 2500 mg per day to about 3000 mg per day, from about 2600 mg per day to about 3000 mg per day, from about 2700 mg per day to about 3000 mg per day, from about 2800 mg per day to about 3000 mg per day, from about 2900 mg per day to about 3000 mg per day, from about 50 mg per day to about 2800 mg per day, from about 100 mg per day to about 2800 mg per day, from about 150 mg per day to about 2800 mg per day, from about 200 mg per day to about 2800 mg per day, from about 300 mg per day to about 2800 mg per day, from about 400 mg per day to about 2800 mg per day, from about 500 mg per day to about 2800 mg per day, from about 600 mg per day to about 2800 mg per day, from about 700 mg per day to about 2800 mg per day, from about 800 mg per day to about 2800 mg per day, from about 900 mg per day to about 2800 mg per day, from about 1000 mg per day to about 2800 mg per day, from about 1100 mg per day to about 2800 mg per day, from about 1200 mg per day to about 2800 mg per day, from about 1300 mg per day to about 2800 mg per day, from about 1400 mg per day to about 2800 mg per day, from about 1500 mg per day to about 2800 mg per day, from about 1600 mg per day to about 2800 mg per day, from about 1700 mg per day to about 2800 mg per day, from about 1800 mg per day to about 2800 mg per day, from about 1900 mg per day to about 2800 mg per day, from about 2000 mg per day to about 2800 mg per day, from about 2100 mg per day to about 2800 mg per day, from about 2200 mg per day to about 2800 mg per day, from about 2300 mg per day to about 2800 mg per day, from about 2400 mg per day to about 2800 mg per day, from about 2500 mg per day to about 2800 mg per day, from about 2600 mg per day to about 2800 mg per day, from about 2700 mg per day to about 2800 mg per day, from about 50 mg per day to about 2500 mg per day, from about 100 mg per day to about 2500 mg per day, from about 150 mg per day to about 2500 mg per day, from about 200 mg per day to about 2500 mg per day, from about 300 mg per day to about 2500 mg per day, from about 400 mg per day to about 2500 mg per day, from about 500 mg per day to about 2500 mg per day, from about 600 mg per day to about 2500 mg per day, from about 700 mg per day to about 2500 mg per day, from about 800 mg per day to about 2500 mg per day, from about 900 mg per day to about 2500 mg per day, from about 1000 mg per day to about 2500 mg per day, from about 1100 mg per day to about 2500 mg per day, from about 1200 mg per day to about 2500 mg per day, from about 1300 mg per day to about 2500 mg per day, from about 1400 mg per day to about 2500 mg per day, from about 1500 mg per day to about 2500 mg per day, from about 1600 mg per day to about 2500 mg per day, from about 1700 mg per day to about 2500 mg per day, from about 1800 mg per day to about 2500 mg per day, from about 1900 mg per day to about 2500 mg per day, from about 2000 mg per day to about 2500 mg per day, from about 2100 mg per day to about 2500 mg per day, from about 2200 mg per day to about 2500 mg per day, from about 2300 mg per day to about 2500 mg per day, from about 2400 mg per day to about 2500 mg per day, from about 50 mg per day to about 2200 mg per day, from about 100 mg per day to about 2200 mg per day, from about 150 mg per day to about 2200 mg per day, from about 200 mg per day to about 2200 mg per day, from about 300 mg per day to about 2200 mg per day, from about 400 mg per day to about 2200 mg per day, from about 500 mg per day to about 2200 mg per day, from about 600 mg per day to about 2200 mg per day, from about 700 mg per day to about 2200 mg per day, from about 800 mg per day to about 2200 mg per day, from about 900 mg per day to about 2200 mg per day, from about 1000 mg per day to about 2200 mg per day, from about 1100 mg per day to about 2200 mg per day, from about 1200 mg per day to about 2200 mg per day, from about 1300 mg per day to about 2200 mg per day, from about 1400 mg per day to about 2200 mg per day, from about 1500 mg per day to about 2200 mg per day, from about 1600 mg per day to about 2200 mg per day, from about 1700 mg per day to about 2200 mg per day, from about 1800 mg per day to about 2200 mg per day, from about 1900 mg per day to about 2200 mg per day, from about 2000 mg per day to about 2200 mg per day, from about 2100 mg per day to about 2200 mg per day, from about 50 mg per day to about 2000 mg per day, from about 100 mg per day to about 2000 mg per day, from about 150 mg per day to about 2000 mg per day, from about 200 mg per day to about 2000 mg per day, from about 300 mg per day to about 2000 mg per day, from about 400 mg per day to about 2000 mg per day, from about 500 mg per day to about 2000 mg per day, from about 600 mg per day to about 2000 mg per day, from about 700 mg per day to about 2000 mg per day, from about 800 mg per day to about 2000 mg per day, from about 900 mg per day to about 2000 mg per day, from about 1000 mg per day to about 2000 mg per day, from about 1100 mg per day to about 2000 mg per day, from about 1200 mg per day to about 2000 mg per day, from about 1300 mg per day to about 2000 mg per day, from about 1400 mg per day to about 2000 mg per day, from about 1500 mg per day to about 2000 mg per day, from about 1600 mg per day to about 2000 mg per day, from about 1700 mg per day to about 2000 mg per day, from about 1800 mg per day to about 2000 mg per day, from about 1900 mg per day to about 2000 mg per day, from about 50 mg per day to about 1800 mg per day, from about 100 mg per day to about 1800 mg per day, from about 150 mg per day to about 1800 mg per day, from about 200 mg per day to about 1800 mg per day, from about 300 mg per day to about 1800 mg per day, from about 400 mg per day to about 1800 mg per day, from about 500 mg per day to about 1800 mg per day, from about 600 mg per day to about 1800 mg per day, from about 700 mg per day to about 1800 mg per day, from about 800 mg per day to about 1800 mg per day, from about 900 mg per day to about 1800 mg per day, from about 1000 mg per day to about 1800 mg per day, from about 1100 mg per day to about 1800 mg per day, from about 1200 mg per day to about 1800 mg per day, from about 1300 mg per day to about 1800 mg per day, from about 1400 mg per day to about 1800 mg per day, from about 1500 mg per day to about 1800 mg per day, from about 1600 mg per day to about 1800 mg per day, from about 1700 mg per day to about 1800 mg per day, from about 50 mg per day to about 1500 mg per day, from about 100 mg per day to about 1500 mg per day, from about 150 mg per day to about 1500 mg per day, from about 200 mg per day to about 1500 mg per day, from about 300 mg per day to about 1500 mg per day, from about 400 mg per day to about 1500 mg per day, from about 500 mg per day to about 1500 mg per day, from about 600 mg per day to about 1500 mg per day, from about 700 mg per day to about 1500 mg per day, from about 800 mg per day to about 1500 mg per day, from about 900 mg per day to about 1500 mg per day, from about 1000 mg per day to about 1500 mg per day, from about 1100 mg per day to about 1500 mg per day, from about 1200 mg per day to about 1500 mg per day, from about 1300 mg per day to about 1500 mg per day, from about 1400 mg per day to about 1500 mg per day, from about 50 mg per day to about 1200 mg per day, from about 100 mg per day to about 1200 mg per day, from about 150 mg per day to about 1200 mg per day, from about 200 mg per day to about 1200 mg per day, from about 300 mg per day to about 1200 mg per day, from about 400 mg per day to about 1200 mg per day, from about 500 mg per day to about 1200 mg per day, from about 600 mg per day to about 1200 mg per day, from about 700 mg per day to about 1200 mg per day, from about 800 mg per day to about 1200 mg per day, from about 900 mg per day to about 1200 mg per day, from about 1000 mg per day to about 1200 mg per day, from about 1100 mg per day to about 1200 mg per day, from about 50 mg per day to about 1000 mg per day, from about 100 mg per day to about 1000 mg per day, from about 150 mg per day to about 1000 mg per day, from about 200 mg per day to about 1000 mg per day, from about 300 mg per day to about 1000 mg per day, from about 400 mg per day to about 1000 mg per day, from about 500 mg per day to about 1000 mg per day, from about 600 mg per day to about 1000 mg per day, from about 700 mg per day to about 1000 mg per day, from about 800 mg per day to about 1000 mg per day, from about 900 mg per day to about 1000 mg per day, from about 50 mg per day to about 800 mg per day, from about 100 mg per day to about 800 mg per day, from about 150 mg per day to about 800 mg per day, from about 200 mg per day to about 800 mg per day, from about 300 mg per day to about 800 mg per day, from about 400 mg per day to about 800 mg per day, from about 500 mg per day to about 800 mg per day, from about 600 mg per day to about 800 mg per day, from about 700 mg per day to about 800 mg per day, from about 50 mg per day to about 600 mg per day, from about 100 mg per day to about 600 mg per day, from about 150 mg per day to about 600 mg per day, from about 200 mg per day to about 600 mg per day, from about 300 mg per day to about 600 mg per day, from about 400 mg per day to about 600 mg per day, from about 500 mg per day to about 600 mg per day, from about 50 mg per day to about 500 mg per day, from about 100 mg per day to about 500 mg per day, from about 150 mg per day to about 500 mg per day, from about 200 mg per day to about 500 mg per day, from about 300 mg per day to about 500 mg per day, from about 400 mg per day to about 500 mg per day, from about 50 mg per day to about 400 mg per day, from about 100 mg per day to about 300 mg per day, from about 100 mg per day to about 200 mg per day, from about 200 mg per day to about 500 mg per day, from about 300 mg per day to about 500 mg per day, or from about 400 mg per day to about 500 mg per day.

In some cases, the dose is about 10 mg per day, about 15 mg per day, about 20 mg per day, about 30 mg per day, about 40 mg per day, about 50 mg per day, about 100 mg per day, about 150 mg per day, about 200 mg per day, about 250 mg per day, about 300 mg per day, about 350 mg per day, about 400 mg per day, about 450 mg per day, about 500 mg per day, about 550 mg per day, about 600 mg per day, about 650 mg per day, about 700 mg per day, about 750 mg per day, about 800 mg per day, about 850 mg per day, about 900 mg per day, about 950 mg per day, about 1000 mg per day, about 1100 mg per day, about 1200 mg per day, about 1300 mg per day, about 1400 mg per day, about 1500 mg per day, about 1600 mg per day, about 1700 mg per day, about 1800 mg per day, about 1900 mg per day, about 2000 mg per day, about 2100 mg per day, about 2200 mg per day, about 2300 mg per day, about 2400 mg per day, about 2500 mg per day, about 2600 mg per day, about 2700 mg per day, about 2800 mg per day, about 2900 mg per day, or about 3000 mg per day.

In some embodiments, Trapidil, a derivative, a metabolite, a prodrug, an analog, or a pharmaceutically acceptable salt thereof is administered as oral, parenteral (e.g., intravenous, subcutaneous, intramuscular), intranasal, buccal, topical, rectal, or transdermal administration. In some instances, Trapidil, a derivative, a metabolite, a prodrug, an analog, or a pharmaceutically acceptable salt thereof is administered as an oral administration. In some cases, Trapidil, a derivative, a metabolite, a prodrug, an analog, or a pharmaceutically acceptable salt thereof is administered as a parenteral (e.g., intravenous, subcutaneous, intramuscular) administration. In other cases, Trapidil, a derivative, a metabolite, a prodrug, an analog, or a pharmaceutically acceptable salt thereof is administered as a transdermal administration.

In some embodiments, Trapidil, a derivative, a metabolite, a prodrug, an analog, or a pharmaceutically acceptable salt thereof is administered orally. In some embodiments, the oral dose ranges from about 10 mg per day to about 3000 mg per day. In some instances, the oral dose range is from about 10 mg per day to about 2900 mg per day, from about 10 mg per day to about 2800 mg per day, from about 10 mg per day to about 2700 mg per day, from about 10 mg per day to about 2600 mg per day, from about 10 mg per day to about 2500 mg per day, from about 10 mg per day to about 2400 mg per day, from about 10 mg per day to about 2300 mg per day, from about 10 mg per day to about 2200 mg per day, from about 10 mg per day to about 2100 mg per day, from about 10 mg per day to about 2000 mg per day, from about 10 mg per day to about 1900 mg per day, from about 10 mg per day to about 1800 mg per day, from about 10 mg per day to about 1700 mg per day, from about 10 mg per day to about 1600 mg per day, from about 10 mg per day to about 1500 mg per day, from about 10 mg per day to about 1400 mg per day, from about 10 mg per day to about 1300 mg per day, from about 10 mg per day to about 1200 mg per day, from about 10 mg per day to about 1100 mg per day, from about 10 mg per day to about 1000 mg per day, from about 10 mg per day to about 950 mg per day, from about 10 mg per day to about 900 mg per day, from about 10 mg per day to about 850 mg per day, from about 10 mg per day to about 800 mg per day, from about 10 mg per day to about 750 mg per day, from about 10 mg per day to about 700 mg per day, from about 10 mg per day to about 650 mg per day, from about 10 mg per day to about 600 mg per day, from about 10 mg per day to about 550 mg per day, from about 10 mg per day to about 500 mg per day, from about 10 mg per day to about 450 mg per day, from about 10 mg per day to about 400 mg per day, from about 10 mg per day to about 350 mg per day, from about 10 mg per day to about 300 mg per day, from about 10 mg per day to about 250 mg per day, from about 10 mg per day to about 200 mg per day, from about 10 mg per day to about 150 mg per day, from about 10 mg per day to about 100 mg per day, from about 50 mg per day to about 3000 mg per day, from about 100 mg per day to about 3000 mg per day, from about 150 mg per day to about 3000 mg per day, from about 200 mg per day to about 3000 mg per day, from about 300 mg per day to about 3000 mg per day, from about 400 mg per day to about 3000 mg per day, from about 500 mg per day to about 3000 mg per day, from about 600 mg per day to about 3000 mg per day, from about 700 mg per day to about 3000 mg per day, from about 800 mg per day to about 3000 mg per day, from about 900 mg per day to about 3000 mg per day, from about 1000 mg per day to about 3000 mg per day, from about 1100 mg per day to about 3000 mg per day, from about 1200 mg per day to about 3000 mg per day, from about 1300 mg per day to about 3000 mg per day, from about 1400 mg per day to about 3000 mg per day, from about 1500 mg per day to about 3000 mg per day, from about 1600 mg per day to about 3000 mg per day, from about 1700 mg per day to about 3000 mg per day, from about 1800 mg per day to about 3000 mg per day, from about 1900 mg per day to about 3000 mg per day, from about 2000 mg per day to about 3000 mg per day, from about 2100 mg per day to about 3000 mg per day, from about 2200 mg per day to about 3000 mg per day, from about 2300 mg per day to about 3000 mg per day, from about 2400 mg per day to about 3000 mg per day, from about 2500 mg per day to about 3000 mg per day, from about 2600 mg per day to about 3000 mg per day, from about 2700 mg per day to about 3000 mg per day, from about 2800 mg per day to about 3000 mg per day, from about 2900 mg per day to about 3000 mg per day, from about 50 mg per day to about 2800 mg per day, from about 100 mg per day to about 2800 mg per day, from about 150 mg per day to about 2800 mg per day, from about 200 mg per day to about 2800 mg per day, from about 300 mg per day to about 2800 mg per day, from about 400 mg per day to about 2800 mg per day, from about 500 mg per day to about 2800 mg per day, from about 600 mg per day to about 2800 mg per day, from about 700 mg per day to about 2800 mg per day, from about 800 mg per day to about 2800 mg per day, from about 900 mg per day to about 2800 mg per day, from about 1000 mg per day to about 2800 mg per day, from about 1100 mg per day to about 2800 mg per day, from about 1200 mg per day to about 2800 mg per day, from about 1300 mg per day to about 2800 mg per day, from about 1400 mg per day to about 2800 mg per day, from about 1500 mg per day to about 2800 mg per day, from about 1600 mg per day to about 2800 mg per day, from about 1700 mg per day to about 2800 mg per day, from about 1800 mg per day to about 2800 mg per day, from about 1900 mg per day to about 2800 mg per day, from about 2000 mg per day to about 2800 mg per day, from about 2100 mg per day to about 2800 mg per day, from about 2200 mg per day to about 2800 mg per day, from about 2300 mg per day to about 2800 mg per day, from about 2400 mg per day to about 2800 mg per day, from about 2500 mg per day to about 2800 mg per day, from about 2600 mg per day to about 2800 mg per day, from about 2700 mg per day to about 2800 mg per day, from about 50 mg per day to about 2500 mg per day, from about 100 mg per day to about 2500 mg per day, from about 150 mg per day to about 2500 mg per day, from about 200 mg per day to about 2500 mg per day, from about 300 mg per day to about 2500 mg per day, from about 400 mg per day to about 2500 mg per day, from about 500 mg per day to about 2500 mg per day, from about 600 mg per day to about 2500 mg per day, from about 700 mg per day to about 2500 mg per day, from about 800 mg per day to about 2500 mg per day, from about 900 mg per day to about 2500 mg per day, from about 1000 mg per day to about 2500 mg per day, from about 1100 mg per day to about 2500 mg per day, from about 1200 mg per day to about 2500 mg per day, from about 1300 mg per day to about 2500 mg per day, from about 1400 mg per day to about 2500 mg per day, from about 1500 mg per day to about 2500 mg per day, from about 1600 mg per day to about 2500 mg per day, from about 1700 mg per day to about 2500 mg per day, from about 1800 mg per day to about 2500 mg per day, from about 1900 mg per day to about 2500 mg per day, from about 2000 mg per day to about 2500 mg per day, from about 2100 mg per day to about 2500 mg per day, from about 2200 mg per day to about 2500 mg per day, from about 2300 mg per day to about 2500 mg per day, from about 2400 mg per day to about 2500 mg per day, from about 50 mg per day to about 2200 mg per day, from about 100 mg per day to about 2200 mg per day, from about 150 mg per day to about 2200 mg per day, from about 200 mg per day to about 2200 mg per day, from about 300 mg per day to about 2200 mg per day, from about 400 mg per day to about 2200 mg per day, from about 500 mg per day to about 2200 mg per day, from about 600 mg per day to about 2200 mg per day, from about 700 mg per day to about 2200 mg per day, from about 800 mg per day to about 2200 mg per day, from about 900 mg per day to about 2200 mg per day, from about 1000 mg per day to about 2200 mg per day, from about 1100 mg per day to about 2200 mg per day, from about 1200 mg per day to about 2200 mg per day, from about 1300 mg per day to about 2200 mg per day, from about 1400 mg per day to about 2200 mg per day, from about 1500 mg per day to about 2200 mg per day, from about 1600 mg per day to about 2200 mg per day, from about 1700 mg per day to about 2200 mg per day, from about 1800 mg per day to about 2200 mg per day, from about 1900 mg per day to about 2200 mg per day, from about 2000 mg per day to about 2200 mg per day, from about 2100 mg per day to about 2200 mg per day, from about 50 mg per day to about 2000 mg per day, from about 100 mg per day to about 2000 mg per day, from about 150 mg per day to about 2000 mg per day, from about 200 mg per day to about 2000 mg per day, from about 300 mg per day to about 2000 mg per day, from about 400 mg per day to about 2000 mg per day, from about 500 mg per day to about 2000 mg per day, from about 600 mg per day to about 2000 mg per day, from about 700 mg per day to about 2000 mg per day, from about 800 mg per day to about 2000 mg per day, from about 900 mg per day to about 2000 mg per day, from about 1000 mg per day to about 2000 mg per day, from about 1100 mg per day to about 2000 mg per day, from about 1200 mg per day to about 2000 mg per day, from about 1300 mg per day to about 2000 mg per day, from about 1400 mg per day to about 2000 mg per day, from about 1500 mg per day to about 2000 mg per day, from about 1600 mg per day to about 2000 mg per day, from about 1700 mg per day to about 2000 mg per day, from about 1800 mg per day to about 2000 mg per day, from about 1900 mg per day to about 2000 mg per day, from about 50 mg per day to about 1800 mg per day, from about 100 mg per day to about 1800 mg per day, from about 150 mg per day to about 1800 mg per day, from about 200 mg per day to about 1800 mg per day, from about 300 mg per day to about 1800 mg per day, from about 400 mg per day to about 1800 mg per day, from about 500 mg per day to about 1800 mg per day, from about 600 mg per day to about 1800 mg per day, from about 700 mg per day to about 1800 mg per day, from about 800 mg per day to about 1800 mg per day, from about 900 mg per day to about 1800 mg per day, from about 1000 mg per day to about 1800 mg per day, from about 1100 mg per day to about 1800 mg per day, from about 1200 mg per day to about 1800 mg per day, from about 1300 mg per day to about 1800 mg per day, from about 1400 mg per day to about 1800 mg per day, from about 1500 mg per day to about 1800 mg per day, from about 1600 mg per day to about 1800 mg per day, from about 1700 mg per day to about 1800 mg per day, from about 50 mg per day to about 1500 mg per day, from about 100 mg per day to about 1500 mg per day, from about 150 mg per day to about 1500 mg per day, from about 200 mg per day to about 1500 mg per day, from about 300 mg per day to about 1500 mg per day, from about 400 mg per day to about 1500 mg per day, from about 500 mg per day to about 1500 mg per day, from about 600 mg per day to about 1500 mg per day, from about 700 mg per day to about 1500 mg per day, from about 800 mg per day to about 1500 mg per day, from about 900 mg per day to about 1500 mg per day, from about 1000 mg per day to about 1500 mg per day, from about 1100 mg per day to about 1500 mg per day, from about 1200 mg per day to about 1500 mg per day, from about 1300 mg per day to about 1500 mg per day, from about 1400 mg per day to about 1500 mg per day, from about 50 mg per day to about 1200 mg per day, from about 100 mg per day to about 1200 mg per day, from about 150 mg per day to about 1200 mg per day, from about 200 mg per day to about 1200 mg per day, from about 300 mg per day to about 1200 mg per day, from about 400 mg per day to about 1200 mg per day, from about 500 mg per day to about 1200 mg per day, from about 600 mg per day to about 1200 mg per day, from about 700 mg per day to about 1200 mg per day, from about 800 mg per day to about 1200 mg per day, from about 900 mg per day to about 1200 mg per day, from about 1000 mg per day to about 1200 mg per day, from about 1100 mg per day to about 1200 mg per day, from about 50 mg per day to about 1000 mg per day, from about 100 mg per day to about 1000 mg per day, from about 150 mg per day to about 1000 mg per day, from about 200 mg per day to about 1000 mg per day, from about 300 mg per day to about 1000 mg per day, from about 400 mg per day to about 1000 mg per day, from about 500 mg per day to about 1000 mg per day, from about 600 mg per day to about 1000 mg per day, from about 700 mg per day to about 1000 mg per day, from about 800 mg per day to about 1000 mg per day, from about 900 mg per day to about 1000 mg per day, from about 50 mg per day to about 800 mg per day, from about 100 mg per day to about 800 mg per day, from about 150 mg per day to about 800 mg per day, from about 200 mg per day to about 800 mg per day, from about 300 mg per day to about 800 mg per day, from about 400 mg per day to about 800 mg per day, from about 500 mg per day to about 800 mg per day, from about 600 mg per day to about 800 mg per day, from about 700 mg per day to about 800 mg per day, from about 50 mg per day to about 600 mg per day, from about 100 mg per day to about 600 mg per day, from about 150 mg per day to about 600 mg per day, from about 200 mg per day to about 600 mg per day, from about 300 mg per day to about 600 mg per day, from about 400 mg per day to about 600 mg per day, from about 500 mg per day to about 600 mg per day, from about 50 mg per day to about 500 mg per day, from about 100 mg per day to about 500 mg per day, from about 150 mg per day to about 500 mg per day, from about 200 mg per day to about 500 mg per day, from about 300 mg per day to about 500 mg per day, from about 400 mg per day to about 500 mg per day, from about 50 mg per day to about 400 mg per day, from about 100 mg per day to about 300 mg per day, from about 100 mg per day to about 200 mg per day, from about 200 mg per day to about 500 mg per day, from about 300 mg per day to about 500 mg per day, or from about 400 mg per day to about 500 mg per day.

In some embodiments, the oral dose is about 10 mg per day, about 15 mg per day, about 20 mg per day, about 30 mg per day, about 40 mg per day, about 50 mg per day, about 100 mg per day, about 150 mg per day, about 200 mg per day, about 250 mg per day, about 300 mg per day, about 350 mg per day, about 400 mg per day, about 450 mg per day, about 500 mg per day, about 550 mg per day, about 600 mg per day, about 650 mg per day, about 700 mg per day, about 750 mg per day, about 800 mg per day, about 850 mg per day, about 900 mg per day, about 950 mg per day, about 1000 mg per day, about 1100 mg per day, about 1200 mg per day, about 1300 mg per day, about 1400 mg per day, about 1500 mg per day, about 1600 mg per day, about 1700 mg per day, about 1800 mg per day, about 1900 mg per day, about 2000 mg per day, about 2100 mg per day, about 2200 mg per day, about 2300 mg per day, about 2400 mg per day, about 2500 mg per day, about 2600 mg per day, about 2700 mg per day, about 2800 mg per day, about 2900 mg per day, or about 3000 mg per day.

In some embodiments, Trapidil, a derivative, a metabolite, a prodrug, an analog, or a pharmaceutically acceptable salt thereof is administered in a single dose. In some embodiments, Trapidil, a derivative, a metabolite, a prodrug, an analog, or a pharmaceutically acceptable salt thereof is administered in several doses, e.g., in 2, 3, 4, 5, 6, or more doses per day. In some embodiments, Trapidil, a derivative, a metabolite, a prodrug, an analog, or a pharmaceutically acceptable salt thereof is administered intravenously or subcutaneously. In such instances, the intravenous or subcutaneous administration dose ranges from about 1 mg/kg body weight to about 10 mg/kg body weight, from about 2 mg/kg body weight to about 10 mg/kg body weight, or from about 4 mg/kg body weight to about 8 mg/kg body weight.

Combination Therapy

Disclosed herein, in some embodiments, is a method of treating extrapyramidal syndromes wherein Trapidil, a derivative, a metabolite, a prodrug, an analog, or a pharmaceutically acceptable salt thereof is administered in combination with an additional therapeutic agent.

In some instances, the additional therapeutic agent comprises an antipsychotic, levodopa, an antidepressant, an anti-cholinergic agent, an antiemetic agent, an anxiolytic agent, an antiepileptic agent, an anti-Parkinson's agent, an anti-malarial agent, or an antihistamine. In some instances, Trapidil, a derivative, a metabolite, a prodrug, an analog, or a pharmaceutically acceptable salt thereof is administered in combination with an antipsychotic, levodopa, an antidepressant, an anti-cholinergic agent, an antiemetic agent, an anxiolytic agent, an antiepileptic agent, an anti-Parkinson's agent, an anti-malarial agent, or an antihistamine. In some cases, Trapidil, a derivative, a metabolite, a prodrug, an analog, or a pharmaceutically acceptable salt thereof is administered in combination with an antipsychotic. In some cases, Trapidil, a derivative, a metabolite, a prodrug, an analog, or a pharmaceutically acceptable salt thereof is administered in combination with levodopa. In some cases, Trapidil, a derivative, a metabolite, a prodrug, an analog, or a pharmaceutically acceptable salt thereof is administered in combination with an antidepressant. In some cases, Trapidil, a derivative, a metabolite, a prodrug, an analog, or a pharmaceutically acceptable salt thereof is administered in combination with an anti-cholinergic agent. In some cases, Trapidil, a derivative, a metabolite, a prodrug, an analog, or a pharmaceutically acceptable salt thereof is administered in combination with an antiemetic agent. In some cases, Trapidil, a derivative, a metabolite, a prodrug, an analog, or a pharmaceutically acceptable salt thereof is administered in combination with an anxiolytic agent. In some cases, Trapidil, a derivative, a metabolite, a prodrug, an analog, or a pharmaceutically acceptable salt thereof is administered in combination with an antiepileptic agent. In some cases, Trapidil, a derivative, a metabolite, a prodrug, an analog, or a pharmaceutically acceptable salt thereof is administered in combination with an anti-Parkinson's agent. In some cases, Trapidil, a derivative, a metabolite, a prodrug, an analog, or a pharmaceutically acceptable salt thereof is administered in combination with an anti-malarial agent. In some cases, Trapidil, a derivative, a metabolite, a prodrug, an analog, or a pharmaceutically acceptable salt thereof is administered in combination with an antihistamine.

In some embodiments, the additional therapeutic agent comprises clonazepam, Ginkgo biloba, clozapine, risperidone, quetiapine, vitamin E, levodopa, benzodiazepines, botulinum toxin, reserpine, tetrabenazine, propranolol, dopamine-depleting agents, ondansetron, zotepine, aripiprazole, zopiclone, zonisamide, trihexyphenidyl (Broflex), biperiden, procyclidine, diazepam, baclofen, tizanidine, carbamazepine, gabapentin, lorazepam, mianserin, cyproheptadine, mirtazapine, benztropin, trihexyphenidyl, carbidopa, ropinirole, pramipexole, bromocriptine, selegiline, rasagiline, ziprasidone, olanzapine, amantadine, valbenazine, dutetrabenazine, or diphenhydramine. In some embodiments, the additional therapeutic agent is administered orally. In some embodiments, the additional therapeutic agent is administered intravenously or subcutaneously.

In some embodiments, Trapidil, a derivative, a metabolite, a prodrug, an analog, or a pharmaceutically acceptable salt thereof, are administered in combination with clonazepam, Ginkgo biloba, clozapine, risperidone, quetiapine, vitamin E, levodopa, benzodiazepines, botulinum toxin, reserpine, tetrabenazine, propranolol, dopamine-depleting agents, ondansetron, zotepine, aripiprazole, zopiclone, zonisamide, trihexyphenidyl (Broflex), biperiden, procyclidine, diazepam, baclofen, tizanidine, carbamazepine, gabapentin, lorazepam, mianserin, cyproheptadine, mirtazapine, benztropin, trihexyphenidyl, carbidopa, ropinirole, pramipexole, bromocriptine, selegiline, rasagiline, ziprasidone, olanzapine, amantadine, valbenazine, dutetrabenazine, or diphenhydramine. In some embodiments, the additional therapeutic agent is administered orally. In some embodiments, the additional therapeutic agent is administered intravenously or subcutaneously.

In some embodiments, Trapidil, a derivative, a metabolite, a prodrug, an analog, or a pharmaceutically acceptable salt thereof and the additional therapeutic agent are administered simultaneously. In some instances, Trapidil, a derivative, a metabolite, a prodrug, an analog, or a pharmaceutically acceptable salt thereof and the additional therapeutic agent are administered sequentially. In some instances, Trapidil, a derivative, a metabolite, a prodrug, an analog, or a pharmaceutically acceptable salt thereof is administered before the additional therapeutic agent. In some instances, Trapidil, a derivative, a metabolite, a prodrug, an analog, or a pharmaceutically acceptable salt thereof is administered after the additional therapeutic agent. In some embodiments, Trapidil, a derivative, a metabolite, a prodrug, an analog, or a pharmaceutically acceptable salt thereof and the additional therapeutic agent are administered in a unified dosage form. In some embodiments, Trapidil, a derivative, a metabolite, a prodrug, an analog, or a pharmaceutically acceptable salt thereof and the additional therapeutic agent are administered in separate dosage forms.

Pharmaceutical Combinations and Formulations

Disclosed herein, in certain embodiments, are pharmaceutical compositions or combinations which comprise Trapidil and an additional therapeutic agent. In some instances, pharmaceutical compositions or combinations are formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients are used as suitable and as understood in the art. A summary of pharmaceutical compositions described herein are found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of a compound described herein, such as, for example, Trapidil and an additional therapeutic agent, with other chemical components, such as carriers, stabilizers, diluents, dispersing agents, suspending agents, thickening agents, and/or excipients. The pharmaceutical composition or combination facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions or combinations also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions or combinations also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some instances, pharmaceutical compositions including a compound described herein are manufactured in a conventional manner, such as, by way of example only, by means of conventional mixing, dissolving, granulating, dragee-making, levigating, emulsifying, encapsulating, entrapping or compression processes.

In some instances, "antifoaming agents" reduce foaming during processing which result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In additional embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of Trapidil and an additional therapeutic agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art.

Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, g, or ng of therapeutic agent per mL, dL, or L of blood serum, absorbed into the bloodstream after administration. As used herein, measurable plasma concentrations are typically measured in ng/ml or g/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

In some embodiments, the compositions or combinations described herein are formulated for administration to a subject via any conventional means including, but not limited to, oral, parenteral (e.g., intravenous, subcutaneous, or intramuscular), buccal, intranasal, rectal or transdermal administration routes. In some embodiments, the composition is formulated for administration in a combined dosage form. In some embodiments, the composition is formulated for administration in a separate dosage forms.

Moreover, the pharmaceutical compositions described herein, which include Trapidil and an additional therapeutic agent are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are added to the tablets or dragee coatings for identification or to characterize different combinations of active compound doses.

Pharmaceutical preparations which are used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of Trapidil and/or an additional therapeutic agent, with one or more pharmaceutical excipients to form a bulk blend composition. When referring to these bulk blend compositions as homogeneous, it is meant that the particles of Trapidil and/or an additional therapeutic agent are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

In some instances, the pharmaceutical solid dosage forms described herein include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of Trapidil and/or an additional therapeutic agent. In another embodiment, some or all of the particles of Trapidil and/or an additional therapeutic agent, are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Trapidil and/or an additional therapeutic agent, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Agoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 $g/cm^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of Trapidil and/or an additional therapeutic agent, from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule is prepared, for example, by placing the bulk blend of the formulation of Trapidil and/or an additional therapeutic agent, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Trapidil and/or an additional therapeutic agent, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with Trapidil and/or an additional therapeutic agent, which sufficiently isolate the compound of any of Trapidil or an additional therapeutic agent, from other non-compatible excipients. Materials compatible with compounds of any of Trapidil or an additional therapeutic agent, are those that delay the release of the compounds of any of Trapidil or an additional therapeutic agent, in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, IF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of Trapidil or an additional therapeutic agent may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In other embodiments, the solid dosage formulations of the compounds of any of Trapidil and/or an additional therapeutic agent, are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of Trapidil and/or an additional therapeutic agent, described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH >7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP psuedolatex with particles <1 m. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH >5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include Trapidil and/or an additional therapeutic agent, are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein.

Examples of such delivery systems include, e.g., polymer-based systems, such as polylactic and polyglycolic acid, plyanhydrides and polycaprolactone; porous matrices, non-polymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, pharmaceutical formulations are provided that include particles of Trapidil and/or an additional therapeutic agent, described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HIPMC K100, HIPMC K4M, HIPMC K15M, HIPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Injectable Formulations

Formulations that include a compound of Trapidil or an additional therapeutic agent, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Additional Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

In some instances, the compounds described herein are also formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Therapeutic Regimens

In some embodiments, the Trapidil pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, Trapidil and an additional therapeutic agent are administered simultaneously, sequentially, or at an interval period of time. In some embodiments, Trapidil and an additional therapeutic agent are administered simultaneously. In some cases, Trapidil and an additional therapeutic agent are administered sequentially. In additional cases, Trapidil and an additional therapeutic agent are administered at an interval period of time (e.g., the first administration of a first pharmaceutical composition (e.g., Trapidil) is on day one followed by an interval of at least 1, 2, 3, 4, 5, or more days prior to the administration of at least a second pharmaceutical composition (e.g., an additional therapeutic agent).

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Detection Methods

In some embodiments, methods of detecting the expression level of one or more markers from the panel described herein include, but are not limited to, Western blots, Northern blots, Southern blots, enzyme-linked immunosorbent assay (ELISA), immunoprecipitation, immunofluorescence, radioimmunoassay, immunocytochemistry, nucleic acid hybridization techniques, nucleic acid reverse transcription methods, nucleic acid amplification methods, or a combination thereof. In some cases, the panel comprises FOSL2, JUN, JUND, ATF3, SREBF2, INSIG1, MVK, MVD, LDLR, HMGCR, ERK, DUSP14, SQSTM1, IER3, CDKN1A, MYC, BCL2, or a combination thereof.

In some embodiments, the expression level of one or more markers described herein is determined at the nucleic acid level. Nucleic acid-based techniques for assessing expression are well known in the art and include, for example, determining the level of marker mRNA in a biological sample. Many expression detection methods use isolated RNA. Any RNA isolation technique that does not select against the isolation of mRNA is utilized for the purification of RNA (see, e.g., Ausubel et al., ed. (1987-1999) *Current Protocols in Molecular Biology* (John Wiley & Sons, New York). Additionally, large numbers of tissue samples are readily processed using techniques well known to those of skill in the art, such as, for example, the single-step RNA isolation process disclosed in U.S. Pat. No. 4,843,155.

As used herein, the term "nucleic acid probe" refers to any molecule that is capable of selectively binding to a specifically intended target nucleic acid molecule, for example, a nucleotide transcript. Suitable methods for synthesizing nucleic acid probes are also described in Caruthers, Science, 230:281-285, (1985). In some instances, probes suitable for use herein include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. In some cases, probes are single stranded. In other cases, probes are double stranded. Exemplary nucleotide analogs include phosphate esters of deoxyadenosine, deoxycytidine, deoxyguanosine, deoxythynidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RNA.

In some cases, a probe used for detection optionally includes a detectable label, such as a radiolabel, fluorescent label, or enzymatic label. See for example Lancaster et al., U.S. Pat. No. 5,869,717. In some embodiments, the probe is fluorescently labeled. Fluorescently labeled nucleotides may be produced by various techniques, such as those described in Kambara et al., Bio/Technol., 6:816-21, (1988); Smith et al., Nucl. Acid Res., 13:2399-2412, (1985); and Smith et al., Nature, 321: 674-679, (1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach, IRL Press, Oxford, (1991); Zuckerman et al., Polynucleotides Res., 15: 5305-5321, (1987); Sharma et al., Polynucleotides Res., 19:3019, (1991); Giusti et al., PCR Methods and Applications, 2:223-227, (1993); Fung et al. (U.S. Pat. No. 4,757,141); Stabinsky (U.S. Pat. No. 4,739, 044); Agrawal et al., Tetrahedron Letters, 31: 1543-1546, (1990); Sproat et al., Polynucleotides Res., 15:4837, (1987); and Nelson et al., Polynucleotides Res., 17:7187-7194, (1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Cuisti et al., supra; Agrawal et al, supra; and Sproat et al., supra.

In some cases, the detectable label attached to the probe is either directly or indirectly detectable. In some embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; alexa; fluorescein; conjugated multi-dyes; Brilliant Yellow; coumarin and derivatives; coumarin, 7-amino-4-methylcoumarin (AMC, Coumarin 120), 7-amino-4-trifluoromethyl-couluarin (Coumaran 151); cyanine dyes; cyanosine; 4,6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothio-cyanatodihydro-stilbene-2,2'-disulfonic acid; 4,4'-diisothio-cyanatostilbene-2,2'-disulfonic acid; 5-[dimethylamino] naphthalene-1-sulfonyl chloride (DNS. dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red;

B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6PG), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N', N'tetramethyl-6-carboxyrhodamine (TAMRA);

tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Labels other than fluorescent labels are contemplated by the invention, including other optically-detectable labels.

Detection of a bound probe may be measured using any of a variety of techniques dependent upon the label used, such as those known to one of skill in the art. Exemplary detection methods include radioactive detection, optical absorbance detection, e.g., UV-visible absorbance detection, optical emission detection, e.g., fluorescence or chemiluminescence. Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993)), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc.

In certain embodiments, the target nucleic acid or nucleic acid ligand or both are quantified using methods known in the art. For example, isolated mRNA are used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a marker, marker described herein above. Hybridization of an mRNA with the probe indicates that the marker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the markers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, marker expression is assessed by quantitative fluorogenic RT-PCR (i.e., the TaqMan System).

Modifications or expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression also comprises using nucleic acid probes in solution.

In some embodiments, microarrays are used to determine expression or presence of one or more markers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992, 6,020,135, 6,033,860, 6,344,316, and U.S. Pat. Application 20120208706. High-density oligonucleotide arrays are particularly useful for determining the gene expression profile for a large number of RNA's in a sample. Exemplary microarray chips include FoundationOne and FoundationOne Heme from Foundation Medicine, Inc; GeneChip® Human Genome U133 Plus 2.0 array from Affymetrix; and Human DiscoveryMAP® 250+v. 2.0 from Myraid RBM.

Techniques for the synthesis of these arrays using mechanical synthesis methods are described in, e.g., U.S. Pat. No. 5,384,261. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. In some embodiments, arrays are packaged in such a manner as to allow for diagnostics or other manipulation of an all-inclusive device.

In some instances, a method for quantitation is quantitative polymerase chain reaction (QPCR). As used herein, "QPCR" refers to a PCR reaction performed in such a way and under such controlled conditions that the results of the assay are quantitative, that is, the assay is capable of quantifying the amount or concentration of a nucleic acid ligand present in the test sample. QPCR is a technique based on the polymerase chain reaction, and is used to amplify and simultaneously quantify a targeted nucleic acid molecule. QPCR allows for both detection and quantification (as absolute number of copies or relative amount when normalized to DNA input or additional normalizing genes) of a specific sequence in a DNA sample. The procedure follows the general principle of PCR, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), (2006)), Heid et al. (Genome Research 986-994, (1996)), Sarnbrook and Russell (Quantitative PCR, Cold Spring Harbor Protocols, (2006)), and Higuchi (U.S. Pat. Nos. 6,171,785 and 5,994,056).

In some embodiments, the expression level is a protein expression and the level of the protein expression of a gene described herein is detected. In some cases, the detection method comprises contacting a biological sample with an antibody that specifically recognizes or specifically binds to a protein (e.g., a protein encoded by FOSL2, JUN, JUND, ATF3, SREBF2, INSIG1, MVK, MVD, LDLR, HMGCR, ERK, DUSP14, SQSTM1, IER3, CDKN1A, MYC, or BCL2 gene). In some cases, the level of the protein expression is determined by immunoassays including, but not limited to, radioimmunoassay, Western blot assay, ELISA, immunofluorescent assay, enzyme immunoassay, immunoprecipitation, chemiluminescent assay, immunohistochemical assay, dot blot assay, and slot blot assay.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include Trapidil, optionally in a composition or in combination with an additional therapeutic agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1—In Vitro and Computational Analyses to Discover Extrapyramidal Syndrome Transcriptomic Signature Gene expression data for drug perturbed cell lines (MCF7, HL60, and PC3) representing over 1000 compounds, including, but not limited to, FDA and internationally approved drugs, were obtained from the public resource Connectivity Map (Lamb, J., The Connectivity Map: using gene-expression signatures to connect small molecules, genes, and disease. *Science*, 2006. 313 (5795): p. 1929-35). Data was quality controlled, standardized, and normalized. Concurrently, the adverse drug reactions of the compounds were tabulated using the drug labels, primary literature, and statistical analysis of the FDA Adverse Even Reporting System (open.fda.gov/data/faers).

Gene expression data for ~400 drugs with known adverse drug reactions were inputted for computational analysis. Drugs were separated into groups that caused extrapyramidal syndromes (such as tardive dyskinesia and akathisia) or not. A machine learning algorithm paired with feature selection was run that found a transcriptomic signature for compounds known to cause extrapyramidal syndromes. This signature has an accuracy in predicting whether a compound has the potential to cause extrapyramidal syndromes (five-fold cross validation, AUROC=0.858). Using randomized labels, the signature was validated as the results were nullified (five-fold cross validation, AUROC=0.552), confirming the accuracy was related to the biological data, not an artifact of the algorithm.

The transcriptomic signature encompassed 433 genes and was, in some instances, related to the increase of ERK signaling activity induced by the compounds causing extrapyramidal syndromes. The upregulated transcription factors and proteins included those related to activator protein 1 (FOS and JUN), cholesterol synthesis and unfolded protein response (SREBF1/2, CEBPB, and UBC) and ERK2. Downregulated transcription factors and proteins were related to cell cycle progression: MYC and BCL2.

The identified in vitro signature is consistent with in vitro and in vivo animal scientific data on the compounds and the associated dyskinesias (Deslauriers, J., et al., Implication of the ERK/MAPK pathway in antipsychotics-induced dopamine D2 receptor upregulation and in the preventive effects of (+/−)-alpha-lipoic acid in SH-SY5Y neuroblastoma cells. Journal of molecular neuroscience, 2014. 52 (3): p. 378-83; Cao, X., et al., Striatal overexpression of DeltaFosB reproduces chronic levodopa-induced involuntary movements. The Journal of neuroscience: the official journal of the Society for Neuroscience, 2010. 30 (21): p. 7335-43; Nguyen, T. V., et al., Differential expression of c-fos and zif268 in rat striatum after haloperidol, clozapine, and amphetamine. Proc Natl Acad Sci USA, 1992. 89 (10): p. 4270-74).

Example 2—In Vitro and Computational Analyses to Elucidate Trapidil as Treatment for Extrapyramidal Syndrome After elucidating the transcriptomic signature of drugs that cause extrapyramidal syndromes, compounds that reverse the transcriptomic signature under the same in vitro conditions when administered by themselves were computationally identified. The computational algorithm scans the same set of transcriptomic data but identifies compounds that maximally and preferentially reverse the 433 identified genes for extrapyramidal syndromes. Of the ~1100 compounds screened, Trapidil was shown to reverse the transcriptomic signatures for the various extrapyramidal syndromes, such as tardive dyskinesia, dyskinesia, akathisia, or drug-induced Parkinsonism.

Example 3—In Vitro and Computational Analyses to Assess Trapidil's Ability to Ameliorate or Reverse the Transcriptomic Signature of Antipsychotics and Dopamine Trapidil was co-administered with compounds known to induce tardive and levodopa-induced dyskinesia to assess Trapidil's qualitative ability to reverse the identified transcriptomic signature when it is induced by an offending compound (or a compound that induces extrapyramidal syndromes such as tardive dyskinesia, dyskinesia, akathisia, or drug-induced Parkinsonism). Table 1 shows the experimental two-perturbation design. Haloperidol and risperidone were tested. Dopamine was chosen as a substitute for levodopa in cell lines (e.g., MCF7) that do not have the necessary enzymes to convert levodopa into dopamine.

TABLE 1

In vitro study design.

| | Vehicle | Trapidil (10 uM) | Trapidil (20 uM) | Trapidil (50 uM) |
|---|---|---|---|---|
| Vehicle | V_V | V_T1 | V_T2 | V_T5 |
| Haloperidol (10 uM) | H_V | H_T1 | H_T2 | H_T5 |
| Risperidone (10 uM) | R_V | R_T1 | R_T2 | R_T5 |
| Dopamine (1 uM) | D_V | D_T1 | D_T2 | D_T5 |

MCF7 cells were used, cells were plated 24 hrs before compound administration, and cells were exposed to compounds for six hours. All conditions were run in triplicate. The dosage for Trapidil was varied in both directions from the original concentration 20 µM. Haloperidol, risperidone, and dopamine concentrations were higher than known physiological concentrations used in treatment in the brain and cerebrospinal fluid (haloperidol 100× of physiological concentration, risperidone 30×, dopamine 100×). Trapidil concentrations were near physiological brain concentrations approved for treatment (~13 µM). In some instances, high concentrations are used in in vitro studies in order to obtain a quick and robust response by cells. In such instances, in vitro results are carried out with multiple concentrations (Trapidil is repeated for three times) and the qualitative trend is assessed.

After compounds were incubated for six hours with MCF7 cells, total RNA was extracted. The mRNA was enriched and sequencing library preparation was completed. The samples were then sequenced on Illumina HiSeq X machines to generate RNA-seq data for assess transcriptional changes. Each sample had a minimum of 20 million reads, with at least 80% of the base pairs having a Q30 score. RNA-seq reads were aligned to the genome using STAR and counted in mRNA regions using HTSeq. Differential expression was determined using DESeq2.

Single perturbation RNA-seq results (H_V, R_V, D_V, and V_T2) were compared to the Connectivity Map dataset for quality control using a distance metric. Haloperidol, dopamine, and Trapidil RNA-seq data were similar to their respective microarray data obtained from the Connectivity Map. The RNA-seq data for Risperidone was found to be similar to the RNA-seq data for haloperidol and risperidone. Both risperidone RNA-seq and microarray data had similarly different genes, but the RNA-seq data had larger magnitude changes and thus the distance metric chose haloperidol as the closer sample.

As a second quality control, the 433 transcriptomic signature for tardive dyskinesia was differentially expressed, which was determined by the RNA-seq data for haloperidol (p=1.57e-54) and risperidone (p=9.20e-32). For assessing whether dopamine RNA-seq data changed genes implicated in levodopa-induced dyskinesia, the dopamine data was compared to RNA-seq expression patterns in a rat model of levodopa-induced dyskinesia (Smith, L. M., et al., Striatal mRNA expression patterns underlying peak dose L-DOPA-induced dyskinesia in the 6-OHDA hemiparkinsonian rat. Neuroscience, 2016. 324: p. 238-51). Concordance was found between the two transcriptomic signatures (p=0.0166) from different experimental conditions (in vitro vs in vivo) and different organisms (human vs rat).

Figure 2:
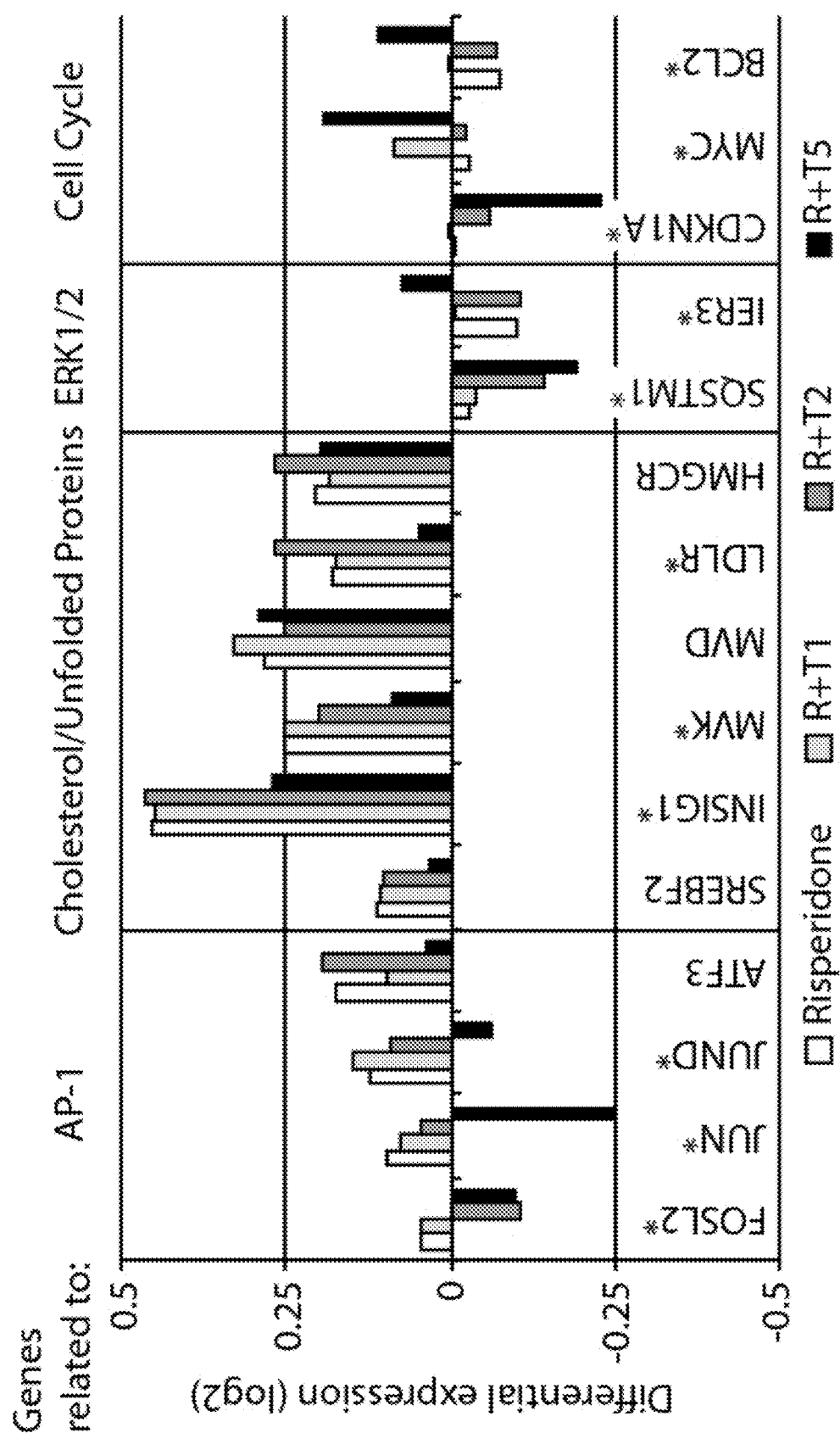
FIG. 2 shows Trapidil's ability to ameliorate or reverse the expression changes in key genes related to extrapyramidal syndromes induced by risperidone, a second generation antipsychotic. * indicates that the change induced by Trapidil was significant at FDR <0.05.

After quality checks, whether Trapidil qualitatively ameliorated or reversed the transcriptomic signature induced by haloperidol and risperidone that was discussed in Example 1 was assessed. In some instances, the transcripts associated with SREBF1, FOS, CEBPB, UBC, ERK2, and JUN were evaluated. In FIG. 1, the differential expression of haloperidol plus various concentrations of Trapidil are shown. In FIG. 2, the differential expression of risperidone plus various concentrations of Trapidil are shown. Near physiological concentrations of Trapidil reduced or flipped the transcriptomic signature induced by high levels of haloperidol. Trapidil reduced or flipped risperidone induce transcriptomic changes. Changes to risperidone were more pronounced, in line with haloperidol being a more potent, first generation antipsychotic. Changes at FDR <0.05 are exemplified by * on the FIG. 1 and FIG. 2. The remaining genes show a qualitative trend for reducing the expression changes induced by the antipsychotics.

Figure 3:
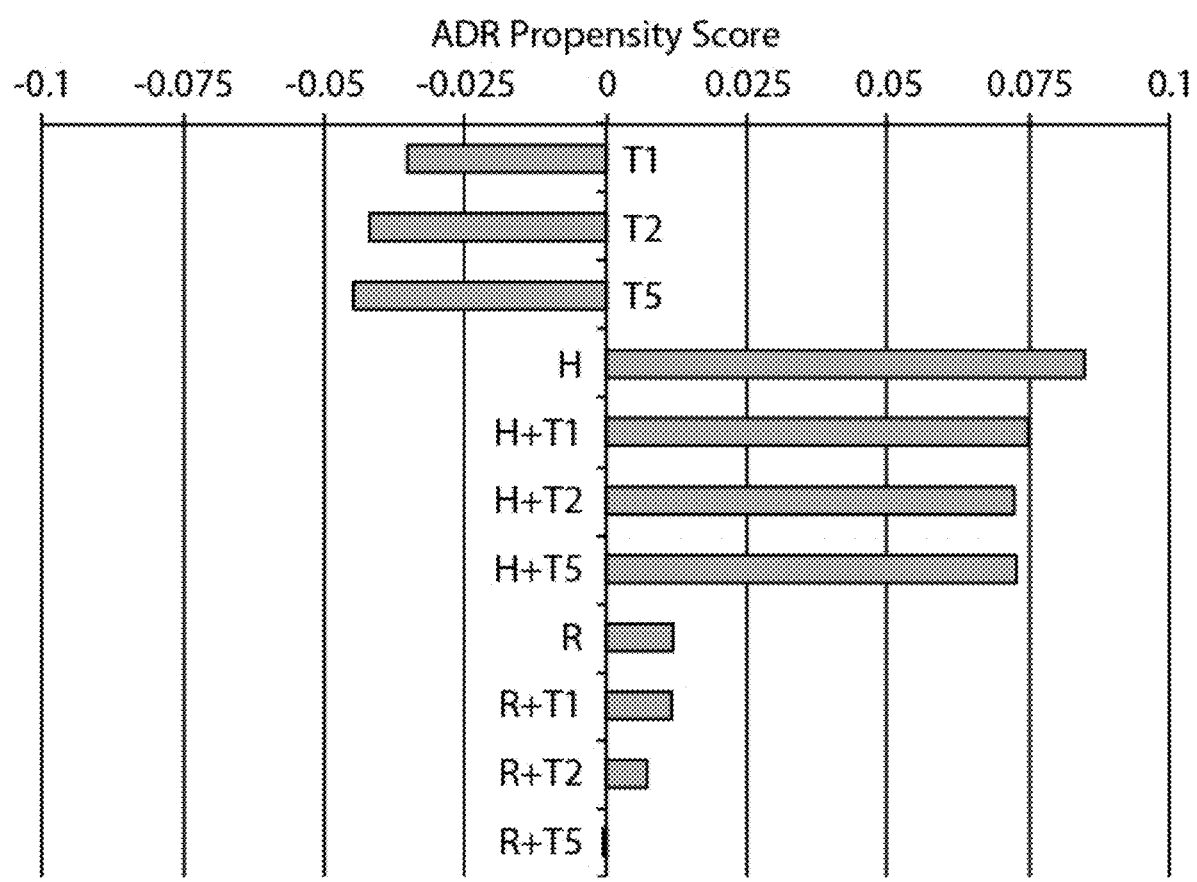
FIG. 3 shows the extrapyramidal syndrome propensity score calculated from changes in gene expression for various compound administrations in vitro. Trapidil dose-dependently decreases the gene expression patterns associated with extrapyramidal syndromes that are induced by first generation and second generation antipsychotics (haloperidol and risperidone).

Further, computational analyses to assess how the entire 433 gene transcriptomic signature changed were applied. The RNA-seq data was analyzed by the machine learning algorithm that determined whether or not a compound causes extrapyramidal syndromes to yield a "propensity score". The "propensity score" is an aggregation of the transcriptomic changes across the entire signature. Compounds scoring less than or equal to zero are predicted to not cause the adverse drug reaction, while drugs with larger and larger positive values have higher chances to cause extrapyramidal syndromes. As seen in FIG. 3, haloperidol is predicted to cause extrapyramidal syndromes at a much higher propensity than risperidone. The addition of Trapidil lowers the adverse drug reaction propensity score for both haloperidol and risperidone. For risperidone with Trapidil at 50 µM, the score drops below zeros.

Figure 4:
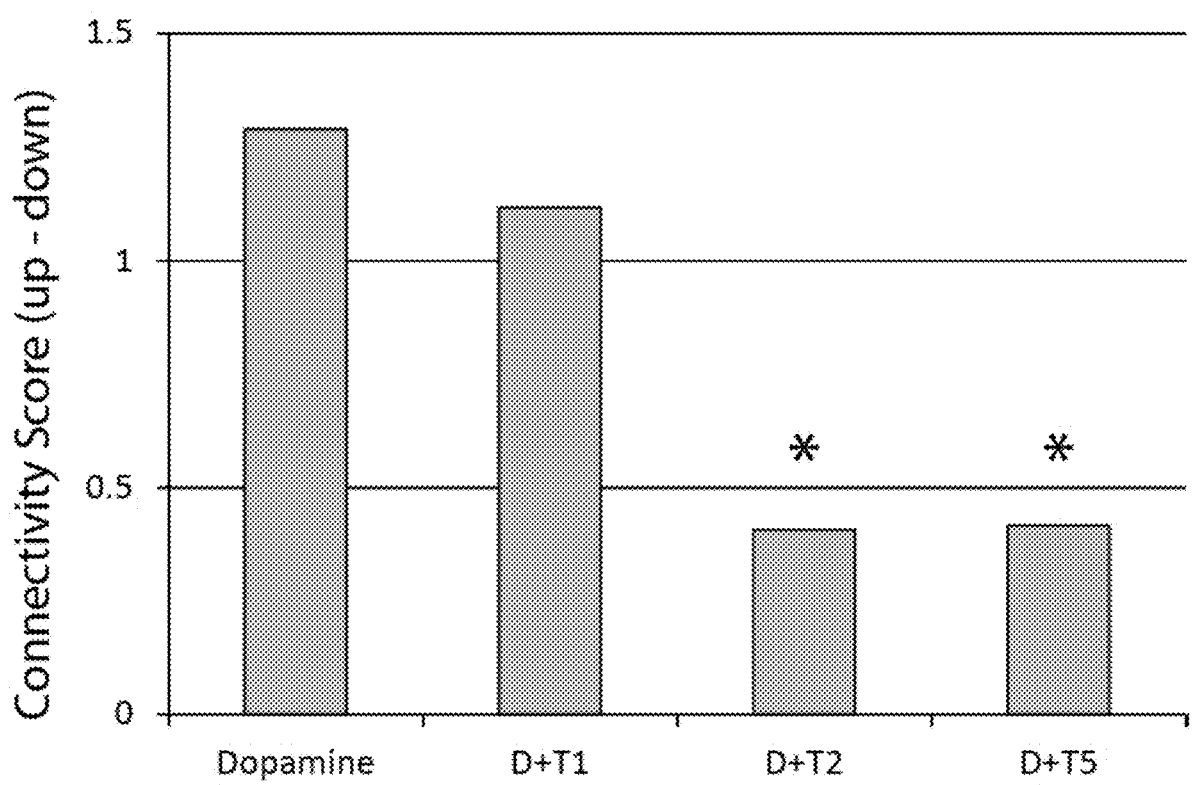
FIG. 4 shows the similarity of gene expression changes induced by compound administrations in vitro to gene expression changes observed in rat striatums in a model of levodopa-induced dyskinesia during levodopa administration. Trapidil dose-dependently changes the gene expression pattern of dopamine away from the dyskinesia transcriptomic signature observed.

To assess Trapidil's effect on levodopa-induced dyskinesia, the transcriptomic signature of dopamine was compared to striatum transcriptomic changes in a rat model of levodopa-induced dyskinesia at peak levodopa levels (Smith, L. M., et al., Striatal mRNA expression patterns underlying peak dose L-DOPA-induced dyskinesia in the 6-OHDA hemiparkinsonian rat. Neuroscience, 2016. 324: p. 238-51). Using the Connectivity Score as a metric of how similar the various gene expression patterns are, it was seen that Trapidil dose dependently decreased the similarity of dopamine's gene expression pattern from the changes noted in the rat brain during levodopa treatment (FIG. 4). The connectivity score is used to assess how similar differential gene expression patterns are, with higher positive scores reflecting similarity and negative scores reflecting opposite expression patterns.

Using gene expression patterns from an in vitro assay, it is observed that Trapidil dose-dependently reduces the gene expression patterns induced by haloperidol, risperidone, and dopamine that are associated with extrapyramidal syndromes, including tardive dyskinesia and levodopa-induced dyskinesia.

Example 4—Initial Dosing Levels of Trapidil and an Antipsychotic for Animal Model Testing Determine plasma and brain pharmacokinetics to characterize dose-exposure relationship: Trapidil is administered to Long-Evans rats through intraperitoneal (IP) injections to measure concentrations in the blood and brain (Table 2).

Initial doses are chosen based on FDA allometric scaling guidance and the current human dosing. The calculated dose (30 mg/kg) is then varied twofold in both directions (15 and 60 mg/kg). Plasma samples are collected at 8 time points to determine PK parameters (Groups 1-3). Based on the resulting plasma profiles, three time points are chosen for determining brain concentration for a 30 mg/kg IP injection of Trapidil (Groups 4-6).

TABLE 2

PK study design and animal numbers.

| Grp | Treatment | Sample Tissue | Assay | # Time Pts | # Rats |
|---|---|---|---|---|---|
| Trapidil Plasma Concentrations | | | | | |
| 1 | T (15 mg/kg) | Plasma | LC-MS/MS | 8 | 3 |
| 2 | T (30 mg/kg) | Plasma | LC-MS/MS | 8 | 3 |
| 3 | T (60 mg/kg) | Plasma | LC-MS/MS | 8 | 3 |

TABLE 2-continued

PK study design and animal numbers.

| Grp | Treatment | Sample Tissue | Assay | # Time Pts | # Rats |
|---|---|---|---|---|---|
| Trapidil Brain Concentrations | | | | | |
| 4 | T (30 mg/kg) | Brain | LC-MS/MS | 1 | 3 |
| 5 | T (30 mg/kg) | Brain | LC-MS/MS | 1 | 3 |
| 6 | T (30 mg/kg) | Brain | LC-MS/MS | 1 | 3 |
| | | Total | | | 18 |

Determine potential drug-drug interaction with antipsychotics to design appropriate dosing strategies: Interactions between Trapidil and antipsychotics are determined by measuring plasma concentrations of the two compounds when administered together versus individually (Table 3). As an example, a first generation antipsychotic haloperidol is shown. Other antipsychotics are studied in a similar fashion, for example for the second generation risperidone.

Haloperidol is administered by a subcutaneously implanted pellet, as continuous administration is more relevant for TD animal models. Haloperidol and Trapidil plasma measurements are made after haloperidol reaches steady state (at 24, 48 hrs, and 72 hrs after implantation) and at 8 time points after IP injection of Trapidil (Table 3). Trapidil concentrations are compared to dosing groups in which the drug was administered individually, while haloperidol concentrations are compared to the initial time points before Trapidil injection to determine any potential drug-drug interaction. In some instances, Trapidil has been shown to modulate CYP1A2, while CYP1A2 has not been shown to interact with haloperidol.

TABLE 3

Testing drug-drug interactions.

| Grp | Treatment | Sample Tissue | Assay | # Time Pts | # Rats |
|---|---|---|---|---|---|
| 7 | T (15 mg/kg) + H (1.5 mg/kg) | Plasma | LC-MS/MS | 12 | 3 |
| 8 | T (30 mg/kg) + H (1.5 mg/kg) | Plasma | LC-MS/MS | 12 | 3 |
| 9 | T (60 mg/kg) + H (1.5 mg/kg) | Plasma | LC-MS/MS | 12 | 3 |
| | | Total | | | 9 |

Example 5—Efficacy of Trapidil in Preventing or Treating Tardive Dyskinesia Using the Established Haloperidol-Induced Dyskinesia Animal Model Using dosages from Example 4, Trapidil is administered to test in vivo efficacy for treatment and prevention of TD. TD like symptoms known as vacuous chewing movements (VCMs) is induced in rodents using antipsychotics. There is a large body of evidence of the applicability of VCMs to TD and haloperidol is most often used for induction. This is done with the established haloperidol-induced dyskinesia rodent model. Though the example is on haloperidol, other antipsychotics can be used to induce VCMs in rats, such as risperidone. The aim is to decrease VCMs by minimum 30% and have powered the study as such (n=10 per group).

Tardive dyskinesia-like symptoms are induced by chronic administration of haloperidol for 10 weeks. This is an established induction method in animals including rats. Early symptoms (~3 weeks) reflect acute extrapyramidal symptoms, while delayed symptoms (~10 weeks) reflect TD. To obtain a human-like haloperidol steady-state concentration, rats are implanted with a subcutaneous slow-release pellet (90-days). This method has been shown to induce reproducible symptoms of TD in rodents with the lowest coefficients of variation compared to oral and injection methods. Previous studies have quantified average number of movements and the standard deviations, and groups of n=10 provide sufficient power to detect a decrease of 30% in TD symptoms.

In this study, age-matched Long-Evans male rats (n=10 per group, ~60 days old) are exposed to continuous administration of haloperidol. Haloperidol induction of orofacial dyskinesia is established in rats as a model of human TD. Long-Evans rats are chosen as they exhibit a more robust response to haloperidol relative to other strains of rats. Continuous administration of haloperidol was chosen over daily injections as symptoms are more pronounced with HAL continuously present.

Figure 5:
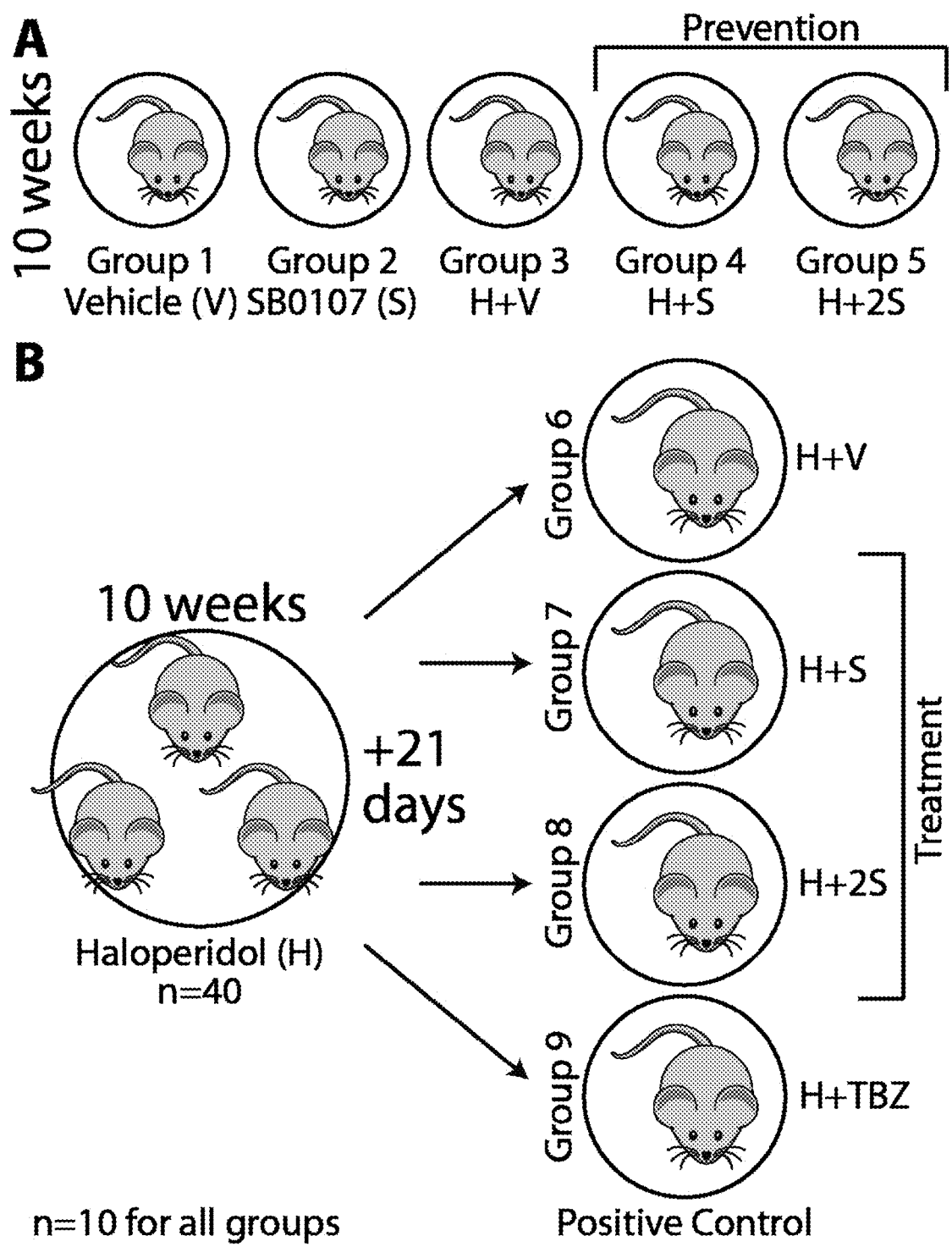
FIG. 5 exemplifies study design for evaluating Trapidil efficacy in treating and/or preventing haloperidol-induced dyskinesia.

The ability of Trapidil to both treat and prevent TD is tested (FIG. 5). For prevention, Trapidil is co-administered with haloperidol over 10 weeks to five groups (FIG. 5A). Dyskinesia symptoms are quantitatively assessed by an observer blinded to the treatment every other week. To test treatment of delayed symptoms, which are more indicative of TD, Trapidil is administered after rats have been treated with haloperidol for 10 weeks. At this point, Trapidil is co-administered at two doses to haloperidol treated groups for 3 weeks and symptoms are monitored every week during this period. It is important to test whether symptoms reduce while still on haloperidol as TD patients typically remain on antipsychotics. The results of this group are compared to rats who have remained 1) just on haloperidol, and 2) haloperidol and a positive control (for example tetrabenazine). Tetrabenazine is administered through IP injection at 5 mg/kg/day, an effective dose in rats for depleting striatal dopamine. For each of these experiments, two different doses of Trapidil are tested: 15 mg/kg/day (T) and 30 mg/kg/day (2T). Additional dosing regiments and concentrations are used to show a dose-dependent response. IP injection vehicles are used to maintain consistency of stress caused by injections across the groups.

Rats are placed in an isolated cage and allowed five minutes to acclimate. The number of VCMs (mouth openings not directed toward physical objects), tongue protrusions and facial jerks are then counted over a 5-minute period. Counts and time is stopped for grooming. Raters will be blinded to treatment condition.

A statistical significant change in VCMs indicates the potential utility of Trapidil in affecting human TD.

Example 6—Efficacy of Trapidil in Preventing or Treating Levodopa-Induced Dyskinesia Using the Established Animal Model Similar to Example 5, dosing for Trapidil is tailored for the Sprague-Dawley rat which is more commonly used for levodopa-induced dyskinesia. Trapidil is administered through IP injections at 15, 30, and 60 m/g/kg to assess plasma concentrations. At selected time point after initial pharmacokinetics profile determination, brain and CSF concentrations are determined.

Similar to Example 5, an established animal model exists for testing the efficacy of Trapidil for levodopa-induced dyskinesia (LID). The 6-OHDA LID rat model is used. (Cenci, M. A., and Lundblad, M., Ratings of L-DOPA-Induced Dyskinesia in the Unilateral 6-OHDA Lesion Model of Parksinson's Disease in Rats and Mice. Current Protocols in Neuroscience, 2007. doi:10.1002/0471142301.ns0925s41). Trapidil is tested to both prevent and/or treat LID. Amantadine is used as a positive control in this example.

Example 7—Clinical Study Trapidil in Tardive Dyskinesia

The purpose of this study is to evaluate the efficacy of Trapidil in Tardive Dyskinesia.
Study Type: Interventional
Allocation: Randomized
Endpoint Classification: Efficacy Study
Intervention Model: Parallel Assignment
Masking: Double Blind (Subject, Investigator, Outcomes Assessor)
Primary Purpose: Treatment
Primary Outcome Measures:
To measure the number of patients with a response to study drug [Time Frame: 8 weeks from first dose]. Participants will be followed until progression of disease. The primary efficacy endpoint is the change in AIMS total score by at least two trained reviewers blinded to the treatment assignment.
Criteria
Inclusion Criteria:
Men and women: age 18-75;
Diagnosis of schizophrenia/schizoaffective disorder according to DSM-IV criteria; diagnosis will be made on the basis of SCID interview and information from medical records, previous treating psychiatrists, and family informants;
History of antipsychotic induced dyskinesia;
History of ≥3 months antipsychotic drugs treatment and present stable dose antipsychotic treatment for at last 4 weeks;
Fulfillment of Schooler-Kane TD research criteria on a first evaluation performed 2-12 weeks prior to study entrance and on a subsequent evaluation performed prior to allocation to experimental treatment;
Subject must have the ability to provide informed consent.
Exclusion Criteria:
Meeting criteria for other DSM-IV Axis I diagnoses;
Presence of a neurological disorder or history of significant head injury;
Substance abuse or alcoholism during entire lifetime;
Are judged clinically to be at suicidal or homicidal risk;
Female patients who are pregnant or lactating; female patients who are not pregnant or lactating, if sexually active, must be using medically accepted means of contraception.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A combination therapy method for treating Parkinson's disease in a subject in need thereof, comprising administering to the subject a combination of:

Trapidil, a derivative, a metabolite, or a pharmaceutically acceptable salt thereof; and levodopa;

thereby treating Parkinson's disease in the subject; wherein the derivative of Trapidil is AR12455
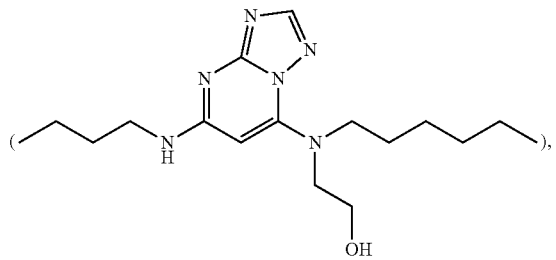

AR12456
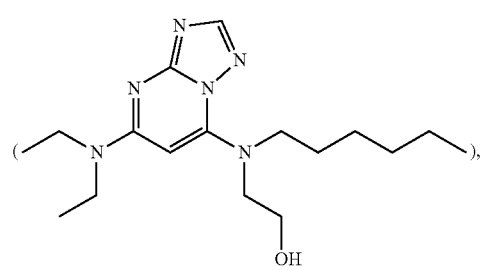

AR12460
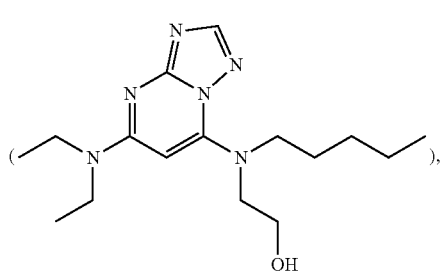

AR12464
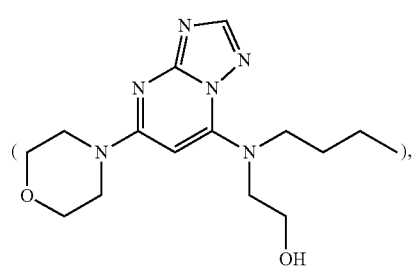

AR12465
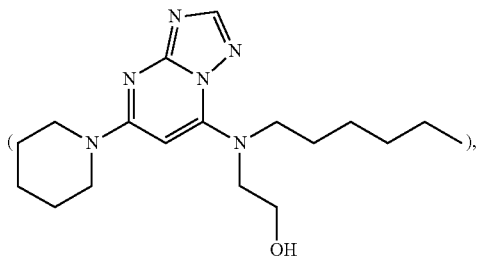

AR12565
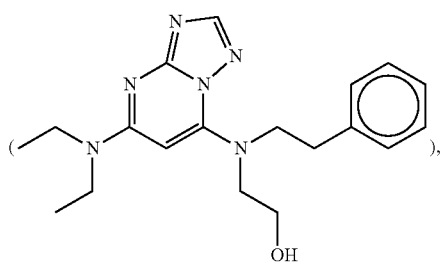

or 5-piperidino-7-(N-(n-amyl)-N-(beta-hydroxyethyl)-amino)-s-triazolo(1,5-a)pyrimidine)

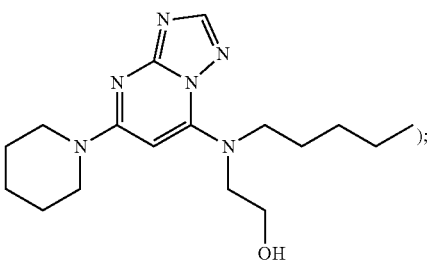 [SMILES: CCCCCN(CCO)c1cc(N2CCCCC2)nc2ncnn12]

wherein the metabolite of Trapidil is TP-1

TP-1
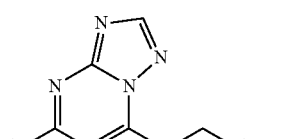 or

TP-2
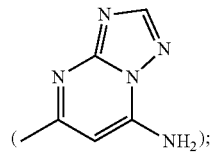;

and wherein the Trapidil is administered in a dose of about 50 mg to about 300 mg.

2. The method of claim 1, wherein the levodopa is formulated with a decarboxylase inhibitor.

3. The method of claim 2, wherein the decarboxylase inhibitor is comprised of carbidopa or benserazide.

4. The method of claim 1, wherein the pharmaceutically acceptable salt of Trapidil comprises a salt with hydrochloric acid, hydrobromic acid, hydroiodic acid, sulfuric acid, nitric acid, oxalic acid, malonic acid, or tartaric acid.

5. The method of claim 1, wherein the Trapidil, the derivative, the metabolite, or the pharmaceutically acceptable salt thereof and the levodopa are administered simultaneously, sequentially, or at an interval period of time.

6. The method of claim 5, wherein the Trapidil, the derivative, the metabolite, or the pharmaceutically acceptable salt thereof is administered prior to administration of the levodopa.

7. The method of claim 5, wherein the Trapidil, the derivative, the metabolite, or the pharmaceutically acceptable salt thereof is administered after administration of the levodopa.

8. The method of claim 1, wherein the Trapidil, the derivative, the metabolite, or the pharmaceutically acceptable salt thereof and the levodopa are administered as a combined dosage form.

9. The method of claim 1, wherein the Trapidil, the derivative, the metabolite, or the pharmaceutically acceptable salt thereof and the levodopa are each independently formulated for oral administration.

10. The method of claim 1, wherein the Trapidil, the derivative, the metabolite, or the pharmaceutically acceptable salt thereof and the levodopa are each independently formulated for parenteral administration.

11. The method of claim 1, wherein the Parkinson's disease is manifested as a dyskinesia, dystonia, akathisia, bradykinesia, tremors, or akinesia.

12. The method of claim 1, wherein the Parkinson's disease is manifested as a dyskinesia.

13. The method of claim 1, wherein the Trapidil, the derivative, the metabolite, or the pharmaceutically acceptable salt thereof potentiate the effect of the levodopa.

14. The method of claim 1, wherein the Trapidil, the derivative, the metabolite, or the pharmaceutically acceptable salt thereof is used as an adjunctive or adjuvant therapeutic agent.

15. The method of claim 1, wherein the subject is a human.

16. The method of claim 1, wherein the dose is from about 50 mg per day to about 1000 mg per day.

17. The method of claim 1, wherein the dose is from about 50 mg per day to about 600 mg per day.

18. The method of claim 1, wherein the dose is from about 50 mg per day to about 400 mg per day.

19. The method of claim 1, wherein the dose is from about 50 mg per day to about 300 mg per day.

20. The method of claim 16, wherein the dose is administered about 5 times per day.

21. The method of claim 17, wherein the dose is administered about 4 times per day.

22. The method of claim 18, wherein the dose is administered about 2 times per day.

23. The method of claim 19, wherein the dose is administered once per day.

* * * * *

UNITED STATES PATENT AND TRADEMARK OFFICE
CERTIFICATE OF CORRECTION

PATENT NO. : 11,628,170 B2
APPLICATION NO. : 16/503128
DATED : April 18, 2023
INVENTOR(S) : Aarash Bordbar It is certified that error appears in the above-identified patent and that said Letters Patent is hereby corrected as shown below:

In the Specification

In Column 3, Line 4, "beta-hydroxyet hyl" should read "beta-hydroxyethyl"

In Column 4, Line 41 and Column 4, Line 42, "beta-hydroxyet hyl" should read "beta-hydroxyethyl"

In Column 5, Line 47, "hydroxyet hyl" should read "beta-hydroxyethyl"

In Column 6, Line 45 and Column 6, Line 46, "beta-hydroxyet hyl" should read "beta-hydroxyethyl"

In Column 12, Line 11, "beta-hydroxyet hyl" should read "beta-hydroxyethyl"

In Column 22, Line 33 and Column 22, Line 34, "beta-hydroxyet hyl" should read "beta-hydroxyethyl"

In Column 23, Line 41, "hydroxyet hyl" should read "beta-hydroxyethyl"

Column 37, Line 29 to Column 37 Line 34, combine the two paragraphs within these lines into one paragraph Column 47, Line 9 to Column 47, Line 32, combine the two paragraphs within these lines into one paragraph Signed and Sealed this
Eighth Day of October, 2024

Katherine Kelly Vidal
*Director of the United States Patent and Trademark Office*